United States Patent
Palmer et al.

(10) Patent No.: US 8,924,878 B2
(45) Date of Patent: Dec. 30, 2014

(54) DISPLAY AND ACCESS TO SETTINGS ON A VENTILATOR GRAPHICAL USER INTERFACE

(75) Inventors: Marc E. Palmer, Trabuco Canyon, CA (US); John P. Skidmore, San Diego, CA (US); Olen D. Porter, Oceanside, CA (US)

(73) Assignee: Covidien LP, Boulder, CO (US)

( * ) Notice: Subject to any disclaimer, the term of this patent is extended or adjusted under 35 U.S.C. 154(b) by 291 days.

(21) Appl. No.: 12/631,750

(22) Filed: Dec. 4, 2009

(65) Prior Publication Data

US 2011/0138308 A1    Jun. 9, 2011

(51) Int. Cl.
*G06F 3/0488* (2013.01)
*G06F 19/00* (2011.01)

(52) U.S. Cl.
CPC .......... *G06F 3/0488* (2013.01); *G06F 19/3406* (2013.01)
USPC ............ 715/771; 715/810; 715/764; 715/760

(58) Field of Classification Search
USPC ......................................... 715/810, 764, 771
See application file for complete search history.

(56) References Cited

U.S. PATENT DOCUMENTS

| | | | |
|---|---|---|---|
| 3,577,984 A | 5/1971 | Levy et al. | |
| 3,659,590 A | 5/1972 | Jones et al. | |
| 3,871,371 A | 3/1975 | Weigl | |
| 3,940,742 A | 2/1976 | Hudspeth et al. | |
| 3,961,624 A | 6/1976 | Weigl | |
| 3,961,627 A | 6/1976 | Ernst et al. | |
| 3,977,394 A | 8/1976 | Jones et al. | |
| 3,991,304 A | 11/1976 | Hillsman | |
| 3,996,928 A | 12/1976 | Marx | |
| 4,034,743 A | 7/1977 | Greenwood et al. | |
| 4,036,217 A | 7/1977 | Ito et al. | |
| 4,053,951 A | 10/1977 | Hudspeth et al. | |
| 4,090,513 A | 5/1978 | Togawa | |
| 4,112,931 A | 9/1978 | Burns | |
| 4,187,842 A | 2/1980 | Schreiber | |

(Continued)

FOREIGN PATENT DOCUMENTS

| | | |
|---|---|---|
| EP | 0414777 | 3/1991 |
| EP | 1374938 | 1/2004 |

(Continued)

OTHER PUBLICATIONS

US 7,284,551, 10/2007, ones et al. (withdrawn).

(Continued)

*Primary Examiner* — Amy Ng
*Assistant Examiner* — Erik Stitt
(74) *Attorney, Agent, or Firm* — Merchant & Gould P.C.

(57) ABSTRACT

This disclosure describes improved systems and methods for displaying, accessing, and changing respiratory settings in a ventilatory system. Specifically, the present disclosure provides for one or more settings access elements, each corresponding to an individual ventilatory setting, for efficiently adjusting displayed ventilatory settings. Access elements may be easily identified as buttons, tabs, icons, or other access displays. After settings have been accessed and changed, pending settings changes may be visually identified on the GUI, or other user interface. In addition, pending settings changes associated with one or more screens of a GUI may be easily identified. Acceptance elements may also be provided which indicate whether one, multiple, or no pending settings changes are available for acceptance.

20 Claims, 8 Drawing Sheets
(8 of 8 Drawing Sheet(s) Filed in Color)

(56) References Cited

U.S. PATENT DOCUMENTS

| | | |
|---|---|---|
| 4,215,409 A | 7/1980 | Strowe |
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,752,089 A | 6/1988 | Carter |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,878,175 A | 10/1989 | Norden-Paul et al. |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,072,737 A | 12/1991 | Goulding |
| 5,137,026 A | 8/1992 | Waterson et al. |
| 5,150,291 A | 9/1992 | Cummings et al. |
| 5,161,525 A | 11/1992 | Kimm et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,253,362 A | 10/1993 | Nolan et al. |
| 5,261,397 A | 11/1993 | Grunstein |
| 5,261,415 A | 11/1993 | Dussault |
| 5,271,389 A | 12/1993 | Isaza et al. |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,319,540 A | 6/1994 | Isaza et al. |
| 5,325,861 A | 7/1994 | Goulding |
| 5,333,106 A | 7/1994 | Lanpher et al. |
| 5,333,606 A | 8/1994 | Schneider et al. |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | Latorraca |
| 5,373,851 A | 12/1994 | Reinhold, Jr. et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,524,615 A | 6/1996 | Power |
| 5,531,221 A | 7/1996 | Power |
| 5,534,851 A | 7/1996 | Russek |
| 5,537,992 A | 7/1996 | Bjoernstijerna et al. |
| 5,542,410 A | 8/1996 | Goodman et al. |
| 5,542,415 A | 8/1996 | Brady |
| 5,544,674 A | 8/1996 | Kelly |
| 5,548,702 A | 8/1996 | Li et al. |
| 5,549,106 A | 8/1996 | Gruenke et al. |
| 5,549,117 A | 8/1996 | Tacklind et al. |
| 5,553,620 A | 9/1996 | Snider |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall |
| 5,611,335 A | 3/1997 | Makhoul et al. |
| 5,626,144 A | 5/1997 | Tacklind et al. |
| 5,630,411 A | 5/1997 | Holscher |
| 5,632,270 A | 5/1997 | O'Mahony et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,645,048 A | 7/1997 | Brodsky et al. |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |

(56) References Cited

U.S. PATENT DOCUMENTS

| | | |
|---|---|---|
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,692,497 A | 12/1997 | Schnitzer et al. |
| 5,697,959 A | 12/1997 | Poore |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,715,812 A | 2/1998 | Deighan et al. |
| 5,724,990 A | 3/1998 | Ogino |
| 5,730,140 A | 3/1998 | Fitch |
| 5,730,145 A | 3/1998 | Defares et al. |
| 5,735,287 A | 4/1998 | Thomson |
| 5,736,974 A * | 4/1998 | Selker .......................... 715/862 |
| 5,738,092 A | 4/1998 | Mock et al. |
| 5,740,792 A | 4/1998 | Ashley et al. |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,762,480 A | 6/1998 | Adahan |
| 5,771,884 A | 6/1998 | Yarnall et al. |
| 5,778,874 A | 7/1998 | Maguire et al. |
| 5,791,339 A | 8/1998 | Winter |
| 5,794,612 A | 8/1998 | Wachter et al. |
| 5,794,986 A | 8/1998 | Gansel et al. |
| 5,800,361 A | 9/1998 | Rayburn |
| 5,806,514 A | 9/1998 | Mock et al. |
| 5,809,997 A | 9/1998 | Wolf |
| 5,813,397 A | 9/1998 | Goodman et al. |
| 5,813,399 A | 9/1998 | Isaza et al. |
| 5,819,723 A | 10/1998 | Joseph |
| 5,822,715 A | 10/1998 | Worthington et al. |
| 5,826,570 A | 10/1998 | Goodman et al. |
| 5,826,575 A | 10/1998 | Lall |
| 5,827,179 A | 10/1998 | Lichter et al. |
| 5,829,441 A | 11/1998 | Kidd et al. |
| 5,839,430 A | 11/1998 | Cama |
| 5,864,938 A | 2/1999 | Gansel et al. |
| 5,865,168 A | 2/1999 | Isaza |
| 5,865,171 A | 2/1999 | Cinquin |
| 5,865,174 A | 2/1999 | Kloeppel |
| 5,875,777 A | 3/1999 | Eriksson |
| 5,878,744 A | 3/1999 | Pfeiffer |
| 5,881,717 A | 3/1999 | Isaza |
| 5,881,723 A | 3/1999 | Wallace |
| 5,884,622 A | 3/1999 | Younes |
| 5,884,623 A | 3/1999 | Winter |
| 5,891,023 A | 4/1999 | Lynn |
| 5,899,203 A | 5/1999 | Defares et al. |
| 5,909,731 A | 6/1999 | O'Mahony et al. |
| 5,915,379 A | 6/1999 | Wallace |
| 5,915,380 A | 6/1999 | Wallace |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,924,418 A | 7/1999 | Lewis |
| 5,931,160 A | 8/1999 | Gilmore |
| 5,932,812 A | 8/1999 | Delsing |
| 5,934,274 A | 8/1999 | Merrick et al. |
| 5,937,854 A | 8/1999 | Stenzler |
| 5,956,501 A | 9/1999 | Brown |
| 5,957,861 A | 9/1999 | Combs et al. |
| 5,971,937 A | 10/1999 | Ekstrom |
| 5,975,081 A | 11/1999 | Hood |
| 5,979,440 A | 11/1999 | Honkonen et al. |
| 5,980,466 A | 11/1999 | Thomson |
| 6,012,450 A | 1/2000 | Rubsamen |
| 6,017,315 A | 1/2000 | Starr |
| 6,024,089 A | 2/2000 | Wallace |
| 6,026,323 A | 2/2000 | Skladnev et al. |
| 6,032,119 A | 2/2000 | Brown et al. |
| 6,041,780 A | 3/2000 | Richard et al. |
| 6,047,860 A | 4/2000 | Sanders |
| 6,055,506 A | 4/2000 | Frasca, Jr. |
| 6,073,110 A | 6/2000 | Rhodes et al. |
| 6,076,523 A | 6/2000 | Jones et al. |
| 6,099,481 A | 8/2000 | Daniels et al. |
| 6,106,481 A | 8/2000 | Cohen |
| 6,116,240 A | 9/2000 | Merrick et al. |
| 6,116,464 A | 9/2000 | Sanders |
| 6,118,847 A | 9/2000 | Hernandez-Guerra |
| 6,119,684 A | 9/2000 | Nohl et al. |
| 6,123,073 A | 9/2000 | Schlawin et al. |
| 6,135,106 A | 10/2000 | Dirks et al. |
| 6,142,150 A | 11/2000 | O'Mahoney |
| 6,148,814 A | 11/2000 | Clemmer et al. |
| 6,148,815 A | 11/2000 | Wolf |
| 6,155,257 A | 12/2000 | Lurie et al. |
| 6,158,432 A | 12/2000 | Biondi |
| 6,159,147 A | 12/2000 | Lichter et al. |
| 6,161,539 A | 12/2000 | Winter |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,955 B1 | 4/2001 | Karakasoglu et al. |
| 6,220,245 B1 | 4/2001 | Takabayashi et al. |
| 6,223,744 B1 | 5/2001 | Garon |
| 6,224,553 B1 | 5/2001 | Nevo |
| 6,233,539 B1 | 5/2001 | Brown |
| 6,234,963 B1 | 5/2001 | Blike et al. |
| 6,240,920 B1 | 6/2001 | Strom |
| 6,251,082 B1 | 6/2001 | Rayburn |
| 6,261,238 B1 | 7/2001 | Gavriely |
| 6,262,728 B1 | 7/2001 | Alexander |
| 6,269,810 B1 | 8/2001 | Brooker et al. |
| 6,269,812 B1 | 8/2001 | Wallace |
| 6,273,088 B1 | 8/2001 | Hillsman |
| 6,273,444 B1 | 8/2001 | Power |
| 6,279,574 B1 | 8/2001 | Richardson et al. |
| 6,283,119 B1 | 9/2001 | Bourdon |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,373 B1 | 10/2001 | Wallace |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,339,410 B1 | 1/2002 | Milner |
| 6,340,348 B1 | 1/2002 | Krishnan |
| 6,342,040 B1 | 1/2002 | Starr |
| 6,349,722 B1 | 2/2002 | Gradon et al. |
| 6,349,724 B1 | 2/2002 | Burton et al. |
| 6,355,002 B1 | 3/2002 | Faram et al. |
| 6,357,438 B1 | 3/2002 | Hansen |
| 6,360,745 B1 | 3/2002 | Wallace |
| 6,362,620 B1 | 3/2002 | Debbins |
| 6,367,475 B1 | 4/2002 | Kofoed et al. |
| 6,369,838 B1 | 4/2002 | Wallace |
| 6,370,419 B1 | 4/2002 | Lampotang |
| 6,377,046 B1 | 4/2002 | Debbins |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,402,698 B1 | 6/2002 | Mault |
| 6,408,043 B1 | 6/2002 | Hu |
| 6,412,483 B1 | 7/2002 | Jones et al. |
| 6,415,792 B1 | 7/2002 | Schoolman |
| 6,416,471 B1 | 7/2002 | Kumar et al. |

(56) References Cited

U.S. PATENT DOCUMENTS

| | | |
|---|---|---|
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |
| 6,439,229 B1 | 8/2002 | Du et al. |
| 6,450,164 B1 | 9/2002 | Banner et al. |
| 6,454,708 B1 | 9/2002 | Ferguson et al. |
| 6,459,933 B1 | 10/2002 | Lurie et al. |
| 6,463,930 B2 | 10/2002 | Biondi et al. |
| 6,467,478 B1 | 10/2002 | Merrick et al. |
| 6,471,658 B1 | 10/2002 | Daniels et al. |
| 6,488,029 B1 | 12/2002 | Toth |
| 6,488,629 B1 | 12/2002 | Saetre |
| RE37,970 E | 1/2003 | Costello, Jr. |
| 6,511,426 B1 | 1/2003 | Hossack |
| 6,512,938 B2 | 1/2003 | Claure |
| 6,515,683 B1 | 2/2003 | Wright |
| 6,517,497 B2 | 2/2003 | Rymut et al. |
| 6,533,723 B1 | 3/2003 | Lockery |
| 6,533,730 B2 | 3/2003 | Strom |
| 6,543,449 B1 | 4/2003 | Woodring |
| 6,543,701 B1 | 4/2003 | Ho |
| 6,544,192 B2 | 4/2003 | Starr |
| 6,546,930 B1 | 4/2003 | Emerson et al. |
| 6,547,728 B1 | 4/2003 | Cornuejols |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,566,875 B1 | 5/2003 | Hasson |
| 6,571,122 B2 | 5/2003 | Schroeppel et al. |
| 6,571,795 B2 | 6/2003 | Bourdon |
| 6,571,796 B2 | 6/2003 | Banner et al. |
| 6,578,575 B1 | 6/2003 | Jonson |
| 6,581,592 B1 | 6/2003 | Bathe et al. |
| 6,584,973 B1 | 7/2003 | Biondi |
| 6,597,939 B1 | 7/2003 | Lampotang |
| 6,599,252 B2 | 7/2003 | Starr |
| 6,603,494 B1 | 8/2003 | Banks |
| 6,606,993 B1 | 8/2003 | Wiesmann et al. |
| 6,620,106 B2 | 9/2003 | Mault |
| 6,621,917 B1 | 9/2003 | Vilser |
| 6,622,726 B1 | 9/2003 | Du |
| 6,629,934 B2 | 10/2003 | Mault et al. |
| 6,630,176 B2 | 10/2003 | Li |
| 6,644,310 B1 | 11/2003 | Delache et al. |
| 6,644,312 B2 | 11/2003 | Berthon-Jones et al. |
| 6,645,158 B2 | 11/2003 | Mault |
| 6,650,346 B1 | 11/2003 | Jaeger |
| 6,651,653 B1 | 11/2003 | Honkonen et al. |
| 6,656,129 B2 | 12/2003 | Niles et al. |
| 6,668,824 B1 | 12/2003 | Isaza et al. |
| 6,668,829 B2 | 12/2003 | Biondi |
| 6,671,529 B2 | 12/2003 | Claure |
| 6,673,018 B2 | 1/2004 | Friedman |
| 6,675,801 B2 | 1/2004 | Wallace |
| 6,679,258 B1 | 1/2004 | Strom |
| 6,681,764 B1 | 1/2004 | Honkonen et al. |
| 6,698,423 B1 | 3/2004 | Honkonen et al. |
| 6,707,476 B1 | 3/2004 | Hochstedler |
| 6,708,688 B1 | 3/2004 | Rubin et al. |
| 6,709,405 B2 | 3/2004 | Jonson |
| 6,712,762 B1 | 3/2004 | Lichter et al. |
| 6,718,974 B1 | 4/2004 | Moberg |
| 6,718,975 B2 | 4/2004 | Blomberg |
| 6,725,077 B1 | 4/2004 | Balloni |
| 6,725,447 B1 | 4/2004 | Gilman et al. |
| 6,725,860 B2 | 4/2004 | Wallroth et al. |
| 6,733,449 B1 | 5/2004 | Krishnamurthy |
| 6,738,079 B1 | 5/2004 | Kellerman et al. |
| 6,739,337 B2 | 5/2004 | Isaza |
| 6,740,046 B2 | 5/2004 | Knapp, II et al. |
| 6,743,172 B1 | 6/2004 | Blike |
| 6,744,374 B1 | 6/2004 | Kuenzner |
| 6,745,764 B2 | 6/2004 | Hickle |
| 6,755,193 B2 | 6/2004 | Berthon-Jones et al. |
| 6,755,787 B2 | 6/2004 | Hossack |
| 6,760,610 B2 | 7/2004 | Tschupp et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg |
| 6,790,178 B1 | 9/2004 | Mault et al. |
| 6,792,066 B1 | 9/2004 | Harder |
| 6,796,305 B1 | 9/2004 | Banner et al. |
| 6,801,227 B2 | 10/2004 | Bocionek |
| 6,801,802 B2 | 10/2004 | Sitzman et al. |
| 6,805,118 B2 | 10/2004 | Brooker et al. |
| 6,807,965 B1 | 10/2004 | Hickle |
| 6,814,074 B1 | 11/2004 | Nadjafizadeh et al. |
| 6,820,614 B2 | 11/2004 | Bonutti |
| 6,820,618 B2 | 11/2004 | Banner et al. |
| 6,822,223 B2 | 11/2004 | Davis |
| 6,824,520 B2 | 11/2004 | Orr et al. |
| 6,828,910 B2 | 12/2004 | VanRyzin et al. |
| 6,830,046 B2 | 12/2004 | Blakley et al. |
| 6,834,647 B2 | 12/2004 | Blair et al. |
| 6,837,242 B2 | 1/2005 | Younes |
| 6,839,753 B2 | 1/2005 | Biondi |
| 6,845,773 B2 | 1/2005 | Berthon-Jones et al. |
| 6,858,006 B2 | 2/2005 | MacCarter et al. |
| 6,860,266 B2 | 3/2005 | Blike |
| 6,866,040 B1 | 3/2005 | Bourdon |
| 6,866,629 B2 | 3/2005 | Bardy |
| 6,893,397 B2 | 5/2005 | Bardy |
| 6,899,103 B1 | 5/2005 | Hood |
| 6,899,683 B2 | 5/2005 | Mault et al. |
| 6,899,684 B2 | 5/2005 | Mault et al. |
| 6,910,481 B2 | 6/2005 | Kimmel et al. |
| 6,921,369 B1 | 7/2005 | Gehrke et al. |
| 6,923,079 B1 | 8/2005 | Snibbe |
| 6,931,269 B2 | 8/2005 | Terry |
| 6,932,083 B2 | 8/2005 | Jones et al. |
| 6,932,767 B2 | 8/2005 | Landry |
| 6,947,780 B2 | 9/2005 | Scharf |
| 6,951,541 B2 | 10/2005 | Desmarais |
| 6,954,702 B2 | 10/2005 | Pierry et al. |
| 6,956,572 B2 | 10/2005 | Zaleski |
| 6,960,854 B2 | 11/2005 | Nadjafizadeh et al. |
| 6,970,919 B1 | 11/2005 | Doi |
| 6,976,958 B2 | 12/2005 | Quy |
| 6,986,347 B2 | 1/2006 | Hickle |
| 6,997,185 B2 | 2/2006 | Han et al. |
| 6,997,880 B2 | 2/2006 | Carlebach et al. |
| 7,006,862 B2 | 2/2006 | Kaufman et al. |
| 7,008,380 B1 | 3/2006 | Rees et al. |
| 7,017,574 B2 | 3/2006 | Biondi |
| 7,019,652 B2 | 3/2006 | Richardson |
| 7,033,323 B2 | 4/2006 | Botbol et al. |
| 7,036,504 B2 | 5/2006 | Wallace |
| 7,039,878 B2 | 5/2006 | Auer |
| 7,040,315 B1 | 5/2006 | Strömberg |
| 7,040,318 B2 | 5/2006 | Däscher et al. |
| 7,040,321 B2 | 5/2006 | Göbel |
| 7,046,254 B2 | 5/2006 | Brown et al. |
| 7,047,092 B2 | 5/2006 | Wimsatt |
| 7,051,736 B2 | 5/2006 | Banner et al. |
| 7,062,251 B2 | 6/2006 | Birkett |
| 7,066,173 B2 | 6/2006 | Banner et al. |
| 7,077,125 B2 | 7/2006 | Scheuch |
| 7,077,131 B2 | 7/2006 | Hansen |
| 7,081,091 B2 | 7/2006 | Merrett et al. |
| 7,081,095 B2 | 7/2006 | Lynn |
| RE39,225 E | 8/2006 | Isaza et al. |
| 7,083,574 B2 | 8/2006 | Kline |
| 7,089,927 B2 | 8/2006 | John et al. |
| 7,089,937 B2 | 8/2006 | Berthon-Jones et al. |
| 7,094,208 B2 | 8/2006 | Williams et al. |
| 7,116,810 B2 | 10/2006 | Miller et al. |
| 7,117,438 B2 * | 10/2006 | Wallace et al. ............... 715/709 |
| 7,128,578 B2 | 10/2006 | Lampotang |
| 7,137,074 B1 | 11/2006 | Newton et al. |
| 7,147,600 B2 | 12/2006 | Bardy |
| 7,156,808 B2 | 1/2007 | Quy |

(56) References Cited

U.S. PATENT DOCUMENTS

| | | | |
|---|---|---|---|
| 7,162,296 B2 | 1/2007 | Leonhardt et al. |
| 7,164,972 B2 | 1/2007 | Imhof et al. |
| 7,165,221 B2 | 1/2007 | Monteleone |
| 7,169,112 B2 | 1/2007 | Caldwell |
| 7,172,557 B1 | 2/2007 | Parker |
| 7,182,083 B2 | 2/2007 | Yanof et al. |
| 7,187,790 B2 | 3/2007 | Sabol |
| 7,188,621 B2 | 3/2007 | DeVries |
| 7,201,734 B2 | 4/2007 | Hickle |
| 7,203,353 B2 | 4/2007 | Klotz |
| 7,210,478 B2 | 5/2007 | Banner et |
| 7,211,049 B2 | 5/2007 | Bradley et |
| 7,219,666 B2 | 5/2007 | Friberg et al. |
| 7,220,230 B2 | 5/2007 | Roteliuk et al. |
| 7,222,054 B2 | 5/2007 | Geva |
| 7,223,965 B2 | 5/2007 | Davis |
| 7,228,323 B2 | 6/2007 | Angerer et al. |
| 7,241,269 B2 | 7/2007 | McCawley et al. |
| 7,246,618 B2 | 7/2007 | Habashi |
| 7,247,154 B2 | 7/2007 | Hickle |
| 7,252,640 B2 | 8/2007 | Ni et al. |
| 7,261,690 B2 | 8/2007 | Teller et al. |
| 7,264,730 B2 | 9/2007 | Connell |
| 7,270,126 B2 | 9/2007 | Wallace |
| 7,275,540 B2 | 10/2007 | Bolam et al. |
| 7,278,579 B2 | 10/2007 | Loffredo |
| 7,282,032 B2 | 10/2007 | Miller |
| 7,285,090 B2 | 10/2007 | Stivoric et al. |
| 7,294,105 B1 | 11/2007 | Islam |
| 7,294,112 B1 | 11/2007 | Dunlop |
| 7,298,280 B2 | 11/2007 | Voege et al. |
| 7,300,418 B2 | 11/2007 | Zaleski |
| 7,303,680 B2 | 12/2007 | Connell |
| 7,308,550 B2 | 12/2007 | Cornett |
| 7,310,551 B1 | 12/2007 | Koh et al. |
| 7,310,720 B2 | 12/2007 | Cornett |
| 7,311,665 B2 | 12/2007 | Hawthorne et al. |
| 7,314,451 B2 | 1/2008 | Halperin et al. |
| 7,316,231 B2 | 1/2008 | Hickle |
| 7,318,808 B2 | 1/2008 | Tarassenko et al. |
| 7,318,892 B2 | 1/2008 | Connell et al. |
| 7,321,802 B2 | 1/2008 | Wasner et al. |
| 7,322,352 B2 | 1/2008 | Minshull et al. |
| 7,322,937 B2 | 1/2008 | Blomberg et al. |
| 7,331,340 B2 | 2/2008 | Barney |
| 7,333,969 B2 | 2/2008 | Lee et al. |
| 7,334,578 B2 | 2/2008 | Biondi et al. |
| 7,343,916 B2 | 3/2008 | Biondi et al. |
| 7,343,917 B2 | 3/2008 | Jones |
| 7,347,200 B2 | 3/2008 | Jones et al. |
| 7,347,207 B2 | 3/2008 | Ahlmen et al. |
| 7,351,340 B2 | 4/2008 | Connell et al. |
| 7,362,341 B2 | 4/2008 | McGuire et al. |
| 7,367,337 B2 | 5/2008 | Berthon-Jones et al. |
| 7,367,955 B2 | 5/2008 | Zhang et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,377,276 B2 | 5/2008 | Roy |
| 7,380,210 B2 | 5/2008 | Lontka et al. |
| RE40,365 E | 6/2008 | Kirchgeorg et al. |
| 7,383,148 B2 | 6/2008 | Ahmed |
| 7,387,610 B2 | 6/2008 | Stahmann et al. |
| 7,413,546 B2 | 8/2008 | Agutter et al. |
| 7,422,562 B2 | 9/2008 | Hatib et al. |
| 7,425,201 B2 | 9/2008 | Euliano et al. |
| 7,428,902 B2 | 9/2008 | Du et al. |
| 7,435,220 B2 | 10/2008 | Ranucci |
| 7,438,072 B2 | 10/2008 | Izuchukwu |
| 7,438,073 B2 | 10/2008 | Delache et al. |
| 7,448,383 B2 | 11/2008 | Delache et al. |
| 7,452,333 B2 | 11/2008 | Roteliuk |
| 7,460,959 B2 | 12/2008 | Jafari |
| 7,464,339 B2 | 12/2008 | Keenan, Jr. et al. |
| 7,469,698 B1 | 12/2008 | Childers et al. |
| 7,487,773 B2 | 2/2009 | Li |
| 7,487,774 B2 | 2/2009 | Acker |
| 7,490,085 B2 | 2/2009 | Walker |
| 7,496,400 B2 | 2/2009 | Hoskonen et al. |
| 7,500,481 B2 | 3/2009 | Delache et al. |
| 7,504,954 B2 | 3/2009 | Spaeder |
| 7,512,450 B2 | 3/2009 | Ahmed |
| 7,512,593 B2 | 3/2009 | Karklins et al. |
| 7,527,053 B2 | 5/2009 | DeVries et al. |
| 7,527,054 B2 | 5/2009 | Misholi |
| 7,530,353 B2 | 5/2009 | Choncholas et al. |
| RE40,806 E | 6/2009 | Gradon et al. |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |

(56) References Cited

U.S. PATENT DOCUMENTS

| | | |
|---|---|---|
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |
| D638,852 S | 5/2011 | Skidmore et al. |
| 7,953,419 B2 | 5/2011 | Jost et al. |
| 7,956,719 B2 | 6/2011 | Anderson, Jr. et al. |
| 7,958,892 B2 | 6/2011 | Kwok et al. |
| 7,970,450 B2 | 6/2011 | Kroecker et al. |
| 7,984,714 B2 | 7/2011 | Hausmann et al. |
| D643,535 S | 8/2011 | Ross et al. |
| 7,990,251 B1 | 8/2011 | Ford, Jr. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,239,780 B2* | 8/2012 | Manetta et al. ............... 715/764 |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0056358 A1 | 12/2001 | Dulong |
| 2002/0026941 A1 | 3/2002 | Biondi et al. |
| 2002/0044059 A1 | 4/2002 | Reeder |
| 2002/0077863 A1 | 6/2002 | Rutledge |
| 2002/0091548 A1 | 7/2002 | Auer |
| 2002/0171682 A1* | 11/2002 | Frank et al. ................... 345/790 |
| 2002/0177758 A1 | 11/2002 | Schoenberg et al. |
| 2003/0060723 A1 | 3/2003 | Joo et al. |
| 2003/0062045 A1* | 4/2003 | Woodring et al. ....... 128/204.18 |
| 2003/0106553 A1 | 6/2003 | Vanderveen |
| 2003/0130567 A1 | 7/2003 | Mault et al. |
| 2003/0130595 A1 | 7/2003 | Mault |
| 2003/0140928 A1 | 7/2003 | Bui et al. |
| 2003/0140929 A1 | 7/2003 | Wilkes et al. |
| 2003/0141368 A1 | 7/2003 | Pascual et al. |
| 2003/0141981 A1 | 7/2003 | Bui et al. |
| 2003/0142138 A1* | 7/2003 | Brown et al. ................. 345/797 |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0208152 A1 | 11/2003 | Avrahami et al. |
| 2003/0208465 A1 | 11/2003 | Yurko |
| 2003/0222548 A1 | 12/2003 | Richardson et al. |
| 2003/0230308 A1 | 12/2003 | Linden |
| 2004/0010425 A1 | 1/2004 | Wilkes et al. |
| 2004/0021693 A1 | 2/2004 | Monteleone |
| 2004/0034289 A1 | 2/2004 | Teller et al. |
| 2004/0059604 A1 | 3/2004 | Zaleski |
| 2004/0073453 A1 | 4/2004 | Nenov |
| 2004/0078231 A1 | 4/2004 | Wilkes et al. |
| 2004/0121767 A1 | 6/2004 | Simpson et al. |
| 2004/0122294 A1 | 6/2004 | Hatlestad et al. |
| 2004/0150525 A1 | 8/2004 | Wilson |
| 2004/0167465 A1 | 8/2004 | Mihai et al. |
| 2004/0167804 A1 | 8/2004 | Simpson et al. |
| 2004/0172222 A1 | 9/2004 | Simpson et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0224293 A1 | 11/2004 | Penning |
| 2004/0236240 A1 | 11/2004 | Kraus et al. |
| 2004/0249673 A1 | 12/2004 | Smith |
| 2005/0016534 A1 | 1/2005 | Ost |
| 2005/0033198 A1 | 2/2005 | Kehyayan et al. |
| 2005/0039748 A1 | 2/2005 | Andrieux |
| 2005/0054910 A1 | 3/2005 | Tremblay et al. |
| 2005/0055242 A1 | 3/2005 | Bello et al. |
| 2005/0055244 A1 | 3/2005 | Mullan et al. |
| 2005/0065817 A1 | 3/2005 | Mihai et al. |
| 2005/0075542 A1 | 4/2005 | Goldreich |
| 2005/0075904 A1 | 4/2005 | Wager |
| 2005/0085869 A1 | 4/2005 | Tehrani |
| 2005/0104860 A1 | 5/2005 | McCreary |
| 2005/0108057 A1 | 5/2005 | Cohen |
| 2005/0112013 A1 | 5/2005 | DeVries et al. |
| 2005/0112325 A1 | 5/2005 | Hickle |
| 2005/0124866 A1 | 6/2005 | Elaz |
| 2005/0133027 A1 | 6/2005 | Elaz |
| 2005/0137480 A1 | 6/2005 | Alt et al. |
| 2005/0139212 A1 | 6/2005 | Bourdon |
| 2005/0139213 A1 | 6/2005 | Blike |
| 2005/0143632 A1 | 6/2005 | Elaz |
| 2005/0156933 A1 | 7/2005 | Lee et al. |
| 2005/0171876 A1 | 8/2005 | Golden |
| 2005/0177096 A1 | 8/2005 | Bollish et al. |
| 2005/0188083 A1 | 8/2005 | Biondi |
| 2005/0192488 A1 | 9/2005 | Bryenton et al. |
| 2005/0204310 A1 | 9/2005 | De Zwart et al. |
| 2005/0215904 A1 | 9/2005 | Sumanaweera |
| 2005/0217674 A1 | 10/2005 | Burton et al. |
| 2005/0251040 A1 | 11/2005 | Relkuntwar |
| 2005/0288571 A1 | 12/2005 | Perkins |
| 2006/0047202 A1 | 3/2006 | Elliott |
| 2006/0078867 A1 | 4/2006 | Penny |
| 2006/0080140 A1 | 4/2006 | Buttner |
| 2006/0080343 A1 | 4/2006 | Carter |
| 2006/0102171 A1 | 5/2006 | Gavish |
| 2006/0122474 A1 | 6/2006 | Teller et al. |
| 2006/0129055 A1 | 6/2006 | Orr et al. |
| 2006/0144396 A1 | 7/2006 | DeVries |
| 2006/0149144 A1 | 7/2006 | Lynn et al. |
| 2006/0149589 A1 | 7/2006 | Wager |
| 2006/0150982 A1 | 7/2006 | Wood |
| 2006/0155183 A1 | 7/2006 | Kroecker |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0174884 A1 | 8/2006 | Habashi |
| 2006/0178911 A1 | 8/2006 | Syed et al. |
| 2006/0189880 A1 | 8/2006 | Lynn et al. |
| 2006/0189900 A1 | 8/2006 | Flaherty |
| 2006/0195041 A1 | 8/2006 | Lynn |
| 2006/0196507 A1 | 9/2006 | Bradley |
| 2006/0200009 A1 | 9/2006 | Wekell et al. |
| 2006/0213518 A1 | 9/2006 | DeVries |
| 2006/0229822 A1 | 10/2006 | Theobald |
| 2006/0235324 A1 | 10/2006 | Lynn |
| 2006/0237015 A1 | 10/2006 | Berthon-Jones et al. |
| 2006/0249151 A1 | 11/2006 | Gambone |
| 2006/0249153 A1 | 11/2006 | DeVries et al. |
| 2006/0264762 A1 | 11/2006 | Starr |
| 2006/0278221 A1 | 12/2006 | Schermeier et al. |
| 2006/0278222 A1 | 12/2006 | Schermeier et al. |
| 2006/0293609 A1 | 12/2006 | Stahmann et al. |
| 2006/0294464 A1 | 12/2006 | Tokimoto et al. |
| 2007/0000490 A1 | 1/2007 | DeVries |
| 2007/0000494 A1 | 1/2007 | Banner et al. |

(56) References Cited

U.S. PATENT DOCUMENTS

| | | |
|---|---|---|
| 2007/0016441 A1 | 1/2007 | Stroup |
| 2007/0017515 A1 | 1/2007 | Wallace |
| 2007/0021673 A1 | 1/2007 | Arbel et al. |
| 2007/0028921 A1 | 2/2007 | Banner et al. |
| 2007/0038081 A1 | 2/2007 | Eck et al. |
| 2007/0060812 A1 | 3/2007 | Harel et al. |
| 2007/0062532 A1 | 3/2007 | Choncholas |
| 2007/0062533 A1 | 3/2007 | Choncholas et al. |
| 2007/0073181 A1 | 3/2007 | Pu |
| 2007/0077200 A1 | 4/2007 | Baker |
| 2007/0113849 A1 | 5/2007 | Matthews |
| 2007/0119453 A1 | 5/2007 | Lu et al. |
| 2007/0123758 A1 | 5/2007 | Miesel et al. |
| 2007/0123792 A1 | 5/2007 | Kline |
| 2007/0129647 A1 | 6/2007 | Lynn |
| 2007/0149860 A1 | 6/2007 | Lynn et al. |
| 2007/0156060 A1 | 7/2007 | Cervantes |
| 2007/0156456 A1 | 7/2007 | McGillin |
| 2007/0157931 A1 | 7/2007 | Parker |
| 2007/0163589 A1 | 7/2007 | DeVries |
| 2007/0179357 A1 | 8/2007 | Bardy |
| 2007/0185390 A1 | 8/2007 | Perkins et al. |
| 2007/0191697 A1 | 8/2007 | Lynn et al. |
| 2007/0199566 A1 | 8/2007 | Be'eri |
| 2007/0208438 A1 | 9/2007 | El-Mankabady et al. |
| 2007/0215155 A1 | 9/2007 | Marx et al. |
| 2007/0225574 A1 | 9/2007 | Ueda |
| 2007/0227537 A1 | 10/2007 | Bemister et al. |
| 2007/0229249 A1 | 10/2007 | McNeal |
| 2007/0241884 A1 | 10/2007 | Yamazaki |
| 2007/0265510 A1 | 11/2007 | Bardy |
| 2007/0265877 A1 | 11/2007 | Rice et al. |
| 2007/0271122 A1 | 11/2007 | Zaleski |
| 2007/0272241 A1 | 11/2007 | Sanborn |
| 2007/0272242 A1 | 11/2007 | Sanborn |
| 2007/0273216 A1 | 11/2007 | Farbarik |
| 2007/0276439 A1 | 11/2007 | Miesel et al. |
| 2007/0284361 A1 | 12/2007 | Nadjafizadeh et al. |
| 2007/0293741 A1 | 12/2007 | Bardy |
| 2008/0000477 A1 | 1/2008 | Huster et al. |
| 2008/0000479 A1 | 1/2008 | Elaz |
| 2008/0007396 A1 | 1/2008 | Parkulo |
| 2008/0022215 A1 | 1/2008 | Lee et al. |
| 2008/0033661 A1 | 2/2008 | Syroid et al. |
| 2008/0039735 A1 | 2/2008 | Hickerson |
| 2008/0041380 A1 | 2/2008 | Wallace |
| 2008/0045844 A1 | 2/2008 | Arbel et al. |
| 2008/0047554 A1 | 2/2008 | Roy |
| 2008/0053438 A1 | 3/2008 | DeVries |
| 2008/0053441 A1 | 3/2008 | Gottlib et al. |
| 2008/0064963 A1 | 3/2008 | Schwaibold et al. |
| 2008/0065420 A1 | 3/2008 | Tirinato |
| 2008/0066753 A1 | 3/2008 | Martin et al. |
| 2008/0072896 A1 | 3/2008 | Setzer |
| 2008/0072900 A1 | 3/2008 | Kenyon et al. |
| 2008/0072901 A1 | 3/2008 | Habashi |
| 2008/0072902 A1* | 3/2008 | Setzer et al. ............. 128/204.21 |
| 2008/0076970 A1 | 3/2008 | Foulis et al. |
| 2008/0077033 A1 | 3/2008 | Figueiredo |
| 2008/0077038 A1 | 3/2008 | McDonough et al. |
| 2008/0077436 A1 | 3/2008 | Muradia |
| 2008/0078390 A1 | 4/2008 | Milne |
| 2008/0083644 A1 | 4/2008 | Janbakhsh et al. |
| 2008/0086691 A1 | 4/2008 | Hopermann et al. |
| 2008/0091122 A1 | 4/2008 | Dunlop |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0103368 A1 | 5/2008 | Craine et al. |
| 2008/0110460 A1 | 5/2008 | Elaz |
| 2008/0125873 A1 | 5/2008 | Payne |
| 2008/0154100 A1 | 6/2008 | Thalmeier et al. |
| 2008/0161653 A1 | 7/2008 | Lin et al. |
| 2008/0172249 A1 | 7/2008 | Glaser-Seidnitzer |
| 2008/0178880 A1 | 7/2008 | Christopher |
| 2008/0178882 A1 | 7/2008 | Christopher |
| 2008/0183057 A1 | 7/2008 | Taube |
| 2008/0185009 A1 | 8/2008 | Choncholas |
| 2008/0205427 A1 | 8/2008 | Jost |
| 2008/0208012 A1 | 8/2008 | Ali |
| 2008/0214947 A1 | 9/2008 | Hunt |
| 2008/0230057 A1 | 9/2008 | Sutherland |
| 2008/0236582 A1 | 10/2008 | Tehrani |
| 2008/0236585 A1 | 10/2008 | Parker |
| 2008/0243016 A1 | 10/2008 | Liao et al. |
| 2008/0251070 A1 | 10/2008 | Pinskiy |
| 2008/0255880 A1 | 10/2008 | Beller |
| 2008/0258929 A1 | 10/2008 | Maschke |
| 2008/0270912 A1 | 10/2008 | Booth |
| 2008/0281219 A1 | 11/2008 | Glickman et al. |
| 2008/0293025 A1 | 11/2008 | Zamierowsi |
| 2008/0295830 A1 | 12/2008 | Martonen |
| 2008/0295839 A1 | 12/2008 | Habashi |
| 2008/0306351 A1 | 12/2008 | Izumi |
| 2008/0308109 A1 | 12/2008 | Brain |
| 2008/0312954 A1 | 12/2008 | Ullrich |
| 2008/0319513 A1 | 12/2008 | Pu |
| 2009/0005651 A1 | 1/2009 | Ward |
| 2009/0007909 A1 | 1/2009 | Carrico |
| 2009/0038921 A1 | 2/2009 | Kaps et al. |
| 2009/0054743 A1 | 2/2009 | Stewart |
| 2009/0055735 A1 | 2/2009 | Zaleski |
| 2009/0062725 A1 | 3/2009 | Goebel |
| 2009/0063181 A1 | 3/2009 | Nho |
| 2009/0065004 A1 | 3/2009 | Childers et al. |
| 2009/0076342 A1 | 3/2009 | Amurthur et al. |
| 2009/0124917 A1 | 5/2009 | Hatlestad et al. |
| 2009/0125333 A1 | 5/2009 | Heywood |
| 2009/0126734 A1 | 5/2009 | Dunsmore |
| 2009/0131758 A1 | 5/2009 | Heywood |
| 2009/0133701 A1 | 5/2009 | Brain |
| 2009/0143694 A1 | 6/2009 | Krauss et al. |
| 2009/0145438 A1 | 6/2009 | Brain |
| 2009/0149200 A1 | 6/2009 | Jayasinghe |
| 2009/0149723 A1 | 6/2009 | Krauss et al. |
| 2009/0149743 A1 | 6/2009 | Barron et al. |
| 2009/0149927 A1 | 6/2009 | Kneuer |
| 2009/0150184 A1 | 6/2009 | Spahn |
| 2009/0165795 A1 | 7/2009 | Nadjafizadeh et al. |
| 2009/0171167 A1 | 7/2009 | Baker, Jr. |
| 2009/0171176 A1 | 7/2009 | Andersohn |
| 2009/0192421 A1 | 7/2009 | Huster et al. |
| 2009/0205661 A1 | 8/2009 | Stephenson et al. |
| 2009/0205663 A1 | 8/2009 | Vandine et al. |
| 2009/0209828 A1 | 8/2009 | Musin |
| 2009/0209849 A1 | 8/2009 | Rowe |
| 2009/0216145 A1 | 8/2009 | Skerl et al. |
| 2009/0221926 A1 | 9/2009 | Younes |
| 2009/0240523 A1 | 9/2009 | Friedlander |
| 2009/0241952 A1 | 10/2009 | Nicolazzi |
| 2009/0241953 A1 | 10/2009 | Vandine et al. |
| 2009/0241956 A1 | 10/2009 | Baker, Jr. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0244003 A1 | 10/2009 | Bonnat |
| 2009/0247891 A1 | 10/2009 | Wood |
| 2009/0249247 A1 | 10/2009 | Tseng et al. |
| 2009/0250054 A1 | 10/2009 | Loncar |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0004517 A1 | 1/2010 | Bryenton et al. |
| 2010/0011307 A1 | 1/2010 | Desfossez et al. |
| 2010/0022904 A1 | 1/2010 | Centen |
| 2010/0024820 A1 | 2/2010 | Bourdon |
| 2010/0030092 A1 | 2/2010 | Kristensen et al. |
| 2010/0048985 A1 | 2/2010 | Henke et al. |
| 2010/0048986 A1 | 2/2010 | Henke et al. |
| 2010/0049034 A1 | 2/2010 | Eck et al. |
| 2010/0049264 A1 | 2/2010 | Henke et al. |
| 2010/0049265 A1 | 2/2010 | Henke et al. |
| 2010/0051026 A1 | 3/2010 | Graboi |

(56) References Cited

U.S. PATENT DOCUMENTS

| | | |
|---|---|---|
| 2010/0051029 A1 | 3/2010 | Jafari et al. |
| 2010/0056852 A1 | 3/2010 | Henke et al. |
| 2010/0056853 A1 | 3/2010 | Henke et al. |
| 2010/0056855 A1 | 3/2010 | Henke et al. |
| 2010/0056929 A1 | 3/2010 | Stahmann et al. |
| 2010/0056941 A1 | 3/2010 | Henke et al. |
| 2010/0056942 A1 | 3/2010 | Henke et al. |
| 2010/0057148 A1 | 3/2010 | Henke et al. |
| 2010/0059061 A1 | 3/2010 | Brain |
| 2010/0063348 A1 | 3/2010 | Henke et al. |
| 2010/0063350 A1 | 3/2010 | Henke et al. |
| 2010/0063365 A1 | 3/2010 | Pisani et al. |
| 2010/0069761 A1 | 3/2010 | Karst et al. |
| 2010/0069774 A1 | 3/2010 | Bingham et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0072055 A1 | 3/2010 | Tanaka et al. |
| 2010/0076278 A1 | 3/2010 | van der Zande et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081890 A1 | 4/2010 | Li et al. |
| 2010/0081955 A1 | 4/2010 | Wood, Jr. et al. |
| 2010/0083968 A1 | 4/2010 | Wondka et al. |
| 2010/0095961 A1 | 4/2010 | Tornesel et al. |
| 2010/0130873 A1 | 5/2010 | Yuen et al. |
| 2010/0139660 A1 | 6/2010 | Adahan |
| 2010/0147303 A1 | 6/2010 | Jafari et al. |
| 2010/0160839 A1 | 6/2010 | Freeman et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0274100 A1 | 10/2010 | Behar et al. |
| 2010/0282259 A1 | 11/2010 | Figueiredo et al. |
| 2010/0288283 A1 | 11/2010 | Campbell et al. |
| 2010/0298718 A1 | 11/2010 | Gilham et al. |
| 2010/0300446 A1 | 12/2010 | Nicolazzi et al. |
| 2010/0312132 A1 | 12/2010 | Wood et al. |
| 2010/0317980 A1 | 12/2010 | Guglielmino |
| 2011/0004489 A1 | 1/2011 | Schoenberg et al. |
| 2011/0009746 A1 | 1/2011 | Tran et al. |
| 2011/0011400 A1 | 1/2011 | Gentner et al. |
| 2011/0015493 A1 | 1/2011 | Koschek |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0054289 A1 | 3/2011 | Derchak et al. |
| 2011/0055720 A1 | 3/2011 | Potter et al. |
| 2011/0098638 A1 | 4/2011 | Chawla et al. |
| 2011/0126151 A1 | 5/2011 | Bean et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0066609 A1 | 3/2012 | Howard et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |

FOREIGN PATENT DOCUMENTS

| | | |
|---|---|---|
| EP | 1421966 | 5/2004 |
| EP | 1464357 | 10/2004 |
| GB | 2319967 | 6/1998 |
| WO | WO9014852 | 12/1990 |
| WO | WO9308534 A1 | 4/1993 |
| WO | WO9312823 A2 | 7/1993 |
| WO | WO9314696 A1 | 8/1993 |
| WO | WO9414374 A1 | 7/1994 |
| WO | WO9508471 A1 | 3/1995 |
| WO | WO9532480 A1 | 11/1995 |
| WO | WO9624285 A1 | 8/1996 |
| WO | WO9720592 A1 | 6/1997 |
| WO | WO9811840 A1 | 3/1998 |
| WO | WO9814116 A2 | 4/1998 |
| WO | WO9829790 A2 | 7/1998 |
| WO | WO9833554 A1 | 8/1998 |
| WO | WO9840014 A1 | 9/1998 |
| WO | WO9841267 A1 | 9/1998 |
| WO | WO9841267 C1 | 9/1998 |
| WO | WO9841269 A1 | 9/1998 |
| WO | WO9841270 A1 | 9/1998 |
| WO | WO9841271 A1 | 9/1998 |
| WO | WO9858219 A1 | 12/1998 |
| WO | WO9903524 A1 | 1/1999 |
| WO | WO9952431 A1 | 10/1999 |
| WO | WO9952437 A1 | 10/1999 |
| WO | WO9959460 A2 | 11/1999 |
| WO | WO9962403 A1 | 12/1999 |
| WO | WO0018293 A1 | 4/2000 |
| WO | WO0019886 A1 | 4/2000 |
| WO | WO0062664 A1 | 10/2000 |
| WO | WO0100264 A1 | 1/2001 |
| WO | WO0100265 A1 | 1/2001 |
| WO | WO0128416 A1 | 4/2001 |
| WO | WO0134022 A1 | 5/2001 |
| WO | WO0245566 A2 | 6/2002 |
| WO | WO02082967 A2 | 10/2002 |

(56) References Cited

FOREIGN PATENT DOCUMENTS

| | | |
|---|---|---|
| WO | WO03015005 A2 | 2/2003 |
| WO | WO03024317 A2 | 3/2003 |
| WO | WO03045493 A2 | 6/2003 |
| WO | WO03053503 A1 | 7/2003 |
| WO | WO03060650 A2 | 7/2003 |
| WO | WO03060651 A2 | 7/2003 |
| WO | WO03075989 A2 | 9/2003 |
| WO | WO03075990 A2 | 9/2003 |
| WO | WO03075991 A1 | 9/2003 |
| WO | WO03084405 A2 | 10/2003 |
| WO | WO2004014216 A2 | 2/2004 |
| WO | WO2004014226 A1 | 2/2004 |
| WO | WO2004032719 A2 | 4/2004 |
| WO | WO2004043254 A1 | 5/2004 |
| WO | WO2005010796 | 2/2005 |
| WO | WO2005024729 A1 | 3/2005 |
| WO | WO2005055825 A1 | 6/2005 |
| WO | WO2005056087 A1 | 6/2005 |
| WO | WO2005069740 A2 | 8/2005 |
| WO | WO2005077260 A1 | 8/2005 |
| WO | WO2005112739 A1 | 12/2005 |
| WO | WO2006008745 A2 | 1/2006 |
| WO | WO2006009830 A2 | 1/2006 |
| WO | WO2006037184 A1 | 4/2006 |
| WO | WO2006050388 A2 | 5/2006 |
| WO | WO2006051466 A1 | 5/2006 |
| WO | WO2006078432 A2 | 7/2006 |
| WO | WO2006094055 A2 | 9/2006 |
| WO | WO2006096080 A1 | 9/2006 |
| WO | WO2006109072 A2 | 10/2006 |
| WO | WO2006123956 A1 | 11/2006 |
| WO | WO2006125986 A1 | 11/2006 |
| WO | WO2006125987 A1 | 11/2006 |
| WO | WO2006125989 A1 | 11/2006 |
| WO | WO2006125990 A1 | 11/2006 |
| WO | WO2006137067 A2 | 12/2006 |
| WO | WO2007033050 A2 | 3/2007 |
| WO | WO2007106804 A2 | 9/2007 |
| WO | WO 2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
PCT International Search Report and Written Opinion in Application PCT/US2010/058131, mailed May 18, 2011, 12 pgs.
PCT International Search Report and Written Opinion in Application PCT/US2010/058132, mailed Mar. 3, 2011, 10 pgs.
PCT International Search Report mailed Apr. 7, 2011, International Application No. PCT/US2010/060871, International Filing Date Dec. 16, 2010, Applicant Nellcor Puritan Bennett Llc, 3 pgs.
U.S. Appl. No. 12/631,685, Office Action mailed Nov. 15, 2011, 22 pgs.
U.S. Appl. No. 12/631,685, Office Action mailed Feb. 29, 2012, 23 pgs.
U.S. Appl. No. 12/631,712, Office Action mailed Nov. 14, 2011, 20 pgs.
U.S. Appl. No. 12/631,712, Office Action mailed Feb. 29, 2012, 22 pgs.
U.S. Appl. No. 12/631,752, Office Action mailed Dec. 8, 2011, 12 pgs.
U.S. Appl. No. 12/760,649, Office Action mailed Jan. 6, 2012, 11 pgs.
U.S. Appl. No. 12/631,685, Advisory Action mailed May 11, 2012, 3 pgs.
U.S. Appl. No. 12/631,712, Advisory Action mailed May 11, 2012, 3 pgs.
U.S. Appl. No. 12/631,752, Notice of Allowance mailed Jun. 11, 2012, 8 pgs.
U.S. Appl. No. 12/631,752, Notice of Allowance mailed Jul. 24, 2012, 8 pgs.
U.S. Appl. No. 12/631,752, Office Action mailed Mar. 15, 2012, 13 pgs.
U.S. Appl. No. 12/760,649, Office Action mailed Jul. 20, 2012, 13 pgs.
U.S. Appl. No. 12/970,696, Office Action mailed Aug. 2, 2012, 12 pgs.
U.S. Appl. No. 12/844,579, Office Action mailed Aug. 30, 2012, 9 pgs.
U.S. Appl. No. 12/844,579, Office Action mailed Dec. 19, 2012, 8 pgs.
U.S. Appl. No. 12/760,649, Advisory Action mailed Sep. 28, 2012, 3 pgs.
U.S. Appl. No. 12/970,696, Notice of Allowance mailed Jan. 15, 2013, 14 pgs.
U.S. Appl. No. 12/844,579, Advisory Action mailed Feb. 14, 2013, 3 pgs.
U.S. Appl. No. 12/844,579, Notice of Allowance mailed Mar. 26, 2013, 6 pgs.

\* cited by examiner

DISPLAY AND ACCESS TO SETTINGS ON A VENTILATOR GRAPHICAL USER INTERFACE

RELATED APPLICATIONS

This application is related to co-owned U.S. patent application Ser. No. 12/631,712, entitled "Display of Respiratory Data on a Ventilator Graphical User Interface," filed Dec. 4, 2009; U.S. patent application Ser. No. 12/631,752 (now U.S. Pat. No. 8,335,992), entitled "Visual Indication of Settings Changes on a Ventilator Graphical User Interface," filed Dec. 4, 2009; U.S. patent application Ser. No. 12/631,685, entitled "Visual Indication of Alarms on a Ventilator Graphical User Interface," filed Dec. 4, 2009; and U.S. patent application Ser. No. 12/760,649, entitled "Quick Initiation of Respiratory Support via a Ventilator User Interface," filed Apr. 15, 2010; the entire disclosures of all of which are hereby incorporated herein by reference.

INTRODUCTION

A ventilator is a device that mechanically helps patients breathe by replacing some or all of the muscular effort required to inflate and deflate the lungs. During ventilation, the ventilator may be configured to display useful information to the clinician and to receive inputs and commands from the clinician via one or more user interfaces, including a graphical user interface (GUI). The inputs and commands may include, inter alia, settings inputs during initial ventilator setup or changes to ventilatory settings during ventilation.

Due to the complexity of ventilators, it may be difficult for a clinician to identify where changes to ventilator settings may be entered or edited. Further, it may be difficult for a clinician to identify settings information on multiple screens and displays of the GUI. Specifically, it may be difficult for a clinician to determine how to access and change settings on the GUI. For instance, a clinician may need to quickly and easily identify an appropriate access screen on the GUI for changing and/or entering settings. In addition, may be difficult for a clinician to recognize whether settings changes have been implemented on the ventilator, or whether the settings changes are still pending.

Display and Access to Settings on a Ventilator Graphical User Interface

This disclosure describes improved systems and methods for displaying, accessing, and changing respiratory settings in a ventilatory system. Specifically, the present disclosure provides for one or more settings access elements, each corresponding to an individual ventilatory setting, for efficiently adjusting displayed ventilatory settings. Access elements may be easily identified as buttons, tabs, icons, or other access displays. After settings have been accessed and changed, pending settings changes may be visually identified on the GUI, or other user interface. In addition, pending settings changes associated with one or more screens of a GUI may be easily identified. Acceptance elements may also be provided which indicate whether one, multiple, or no pending settings changes are available for acceptance.

Specifically, a graphical user interface for accessing and displaying ventilatory settings may be provided comprising at least one window associated with the graphical user interface and one or more elements within the at least one window. The one or more elements may further comprise one or more actual ventilatory settings and/or a setup icon. The one or more actual ventilatory settings and/or the setup icon may further be selectable and, upon selection, one or more settings elements may be accessed. A settings element of the one or more settings elements may then be selected, wherein an actual setting value is associated with the selected settings element. The actual setting value may then be changed to a pending setting value that is different from the actual setting value. Thereafter, the pending setting value may be accepted, becoming a changed actual setting value, and the changed actual setting value may populate a corresponding actual ventilatory setting of the one or more actual ventilatory settings.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment having graphical user interfaces for displaying and accessing settings.

This disclosure describes systems and methods for displaying and accessing ventilatory settings. Specifically, a number of settings access elements may be provided, each corresponding to an individual ventilatory setting. The settings access elements may allow a clinician to efficiently access and change displayed ventilatory settings. After settings have been accessed and changed, pending settings changes may be visually identified on the GUI, or other user interface. In addition, pending settings changes associated with one or more screens of a GUI may be easily identified. Acceptance elements may also be provided which indicate whether one, multiple, or no pending settings changes are available for acceptance.

Figure 1:
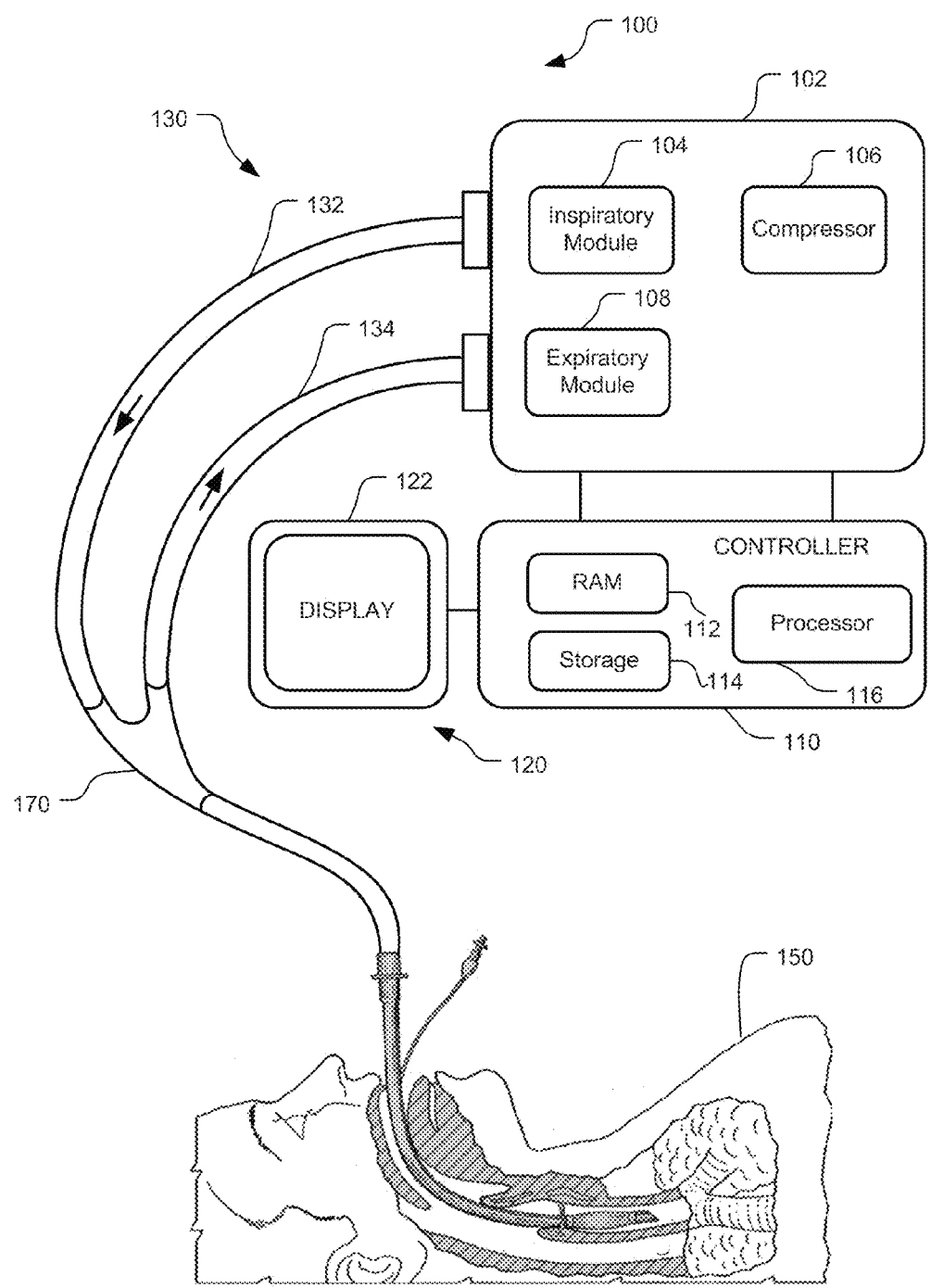
FIG. 1 is a diagram illustrating an embodiment of an exemplary ventilator connected to a human patient.

FIG. 1 illustrates an embodiment of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive patient interface.

Ventilation tubing system 130 may be a two-limb (shown) or a one-limb circuit for carrying gas to and from the patient 150. In a two-limb embodiment as shown, a fitting, typically referred to as a "wye-fitting" 170, may be provided to couple the patient interface to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., reset alarms, change ventilator settings, select operational modes, view monitored parameters, etc.). Controller 110 may include memory 112, one or more processors 116, storage 114, and/or other components of the type commonly found in command and control computing devices.

The memory 112 is computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to evaluate the condition of the patient and to ensure proper functioning of the ventilator according to respiratory settings. The specific monitoring may be based on settings inputs received from pneumatic system 102 and sensors, operator interface 120, and/or other components of the ventilator. In the depicted example, operator interface includes a display 122 that is touch-sensitive, enabling the display to serve both as an input and output device.

Figure 2:
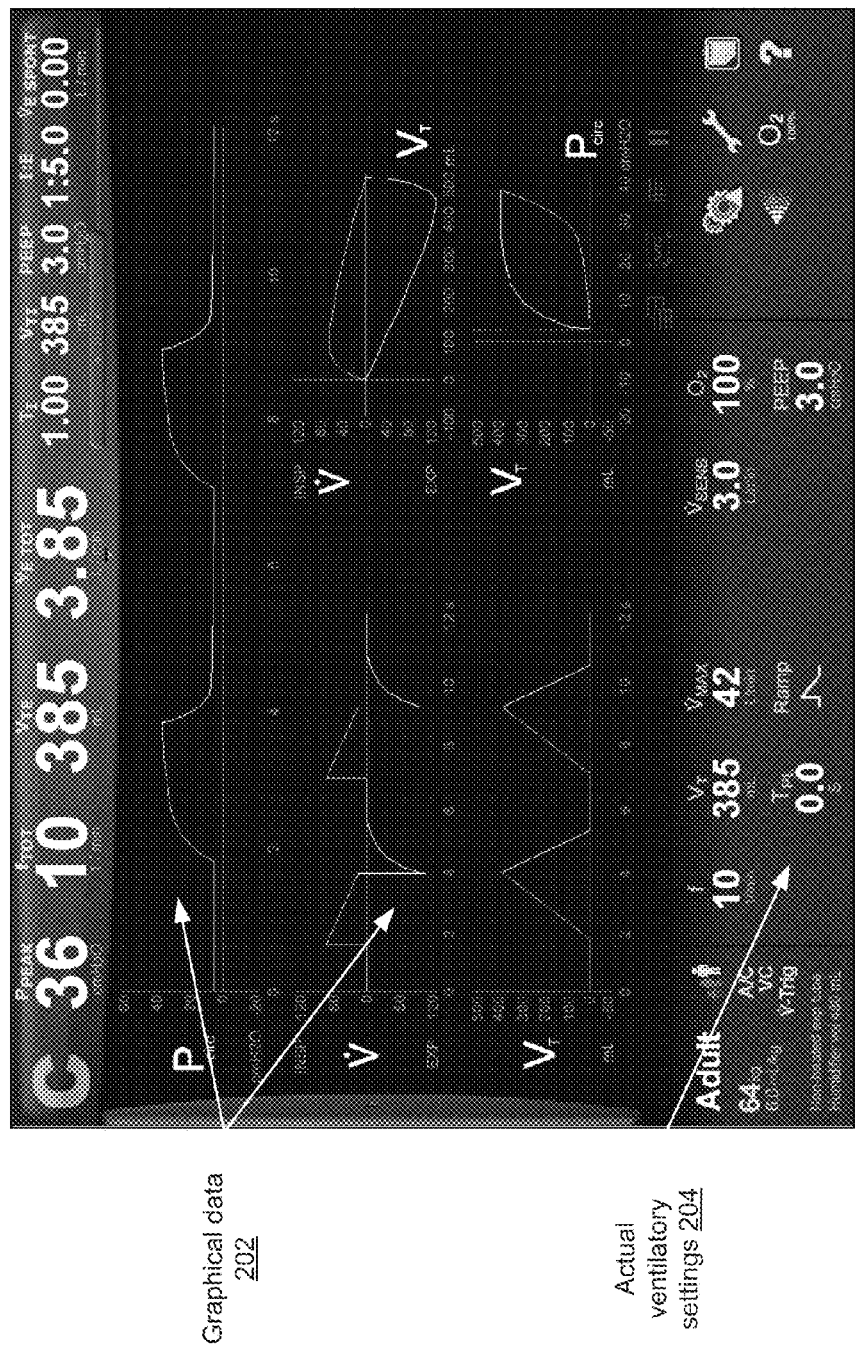
FIG. 2 is an illustration of an embodiment of a graphical user interface displaying graphical respiratory data and current respiratory settings.

FIG. 2 is an illustration of an embodiment of a graphical user interface displaying graphical respiratory data and current ventilatory settings.

For example, the graphical user interface (GUI) may display graphical respiratory data 202. Graphical respiratory data 202 may include, for instance, graphs, wave representations, pie graphs, or other suitable forms of graphical display. Examples of such graphic representations may include, but are not limited to, pressure waveforms, flow waveforms, flow-volume loops, pressure-volume loops, etc. Indeed, in keeping with the spirit of the present disclosure, any graphical or other data display that may be provided by the ventilator based on current respiratory settings may be displayed as graphical data 202.

In addition, the GUI may provide actual ventilatory settings 204. Actual ventilatory settings 204 may refer to any ventilatory setting applicable to the proper functioning of the ventilator and/or the appropriate monitoring of a patient. Actual ventilatory settings 204 may refer to those settings currently implemented by the ventilator. The GUI may be further configured to represent the actual ventilatory settings 204 in a particular font color such that a clinician may be alerted that the settings are being currently implemented by the ventilator. For example, the actual ventilatory settings 204 may be presented in a white font.

Actual ventilatory settings 204 may include settings for frequency, tidal volume, maximum and minimum flow, FiO2, PEEP, etc., as illustrated in FIG. 2. However, as noted above, actual ventilatory settings 204 may display any configurable ventilatory setting that may be useful to a clinician.

By way of example, actual ventilatory settings 204 may include a variety of settings for governing the proper delivery of ventilation to a patient. For example, a setting for frequency, f, may be provided (as illustrated, 10 breaths per minute). Frequency refers to a number of breaths over a period of time that should be delivered by the ventilator to the patient. By way of another example, a setting for tidal volume, $V_T$, may be provided (as illustrated, 385 mL). Tidal volume refers to the total volume of air inhaled and exhaled for one respiratory cycle. As such, the ventilator may be configured with a tidal volume setting to ensure that the patient receives and exhales an adequate volume of air. One or more settings for flow may also be provided (as illustrated, maximum flow set to 42 L/min). Flow refers to circuit airflow into and out of a patient's lungs and is governed by a pressure gradient between the lungs and external atmospheric pressure. As very high flow may cause damage to a patient's lungs, trachea, etc., and an extremely low flow may indicate a leak or other unsafe condition, flow settings may include a maximum flow and a minimum flow, for example. A fractional inspired oxygen ($FiO_2$) setting may also be provided (as illustrated, 100%). $FiO_2$ refers to a percent of oxygen delivered to the patient, e.g., ranging from 21% (room air) to 100%. A setting for positive end-expiratory pressure (PEEP) may be included as well (as illustrated, 3.0 $H_2O$). During each breath, air is delivered by the ventilator to the patient's lungs, which results in a net increase in pressure (e.g., in cm $H_2O$). Pressure may be delivered from a non-zero baseline pressure, for instance, a baseline pressure above zero cm $H_2O$ is referred to as positive-end expiratory pressure or PEEP. When the ventilator includes a PEEP setting, the patient is prevented from exhaling to zero cm $H_2O$, or atmospheric pressure. Thus, PEEP increases the volume of air left in the lungs at the end of expiration.

The above-described ventilatory settings may be configured according to any suitable means, for instance according to safety standards, clinical studies, or other applicable protocols or specifications. Additionally, as will be described further herein, actual ventilatory settings 204 may be changed or adjusted based on the condition of the patient, or other considerations. Only a sampling of the illustrated actual ventilatory settings 204 have been defined and described, but the described ventilatory settings are characteristic of ventilatory settings that may be configured and displayed via actual ventilatory settings 204. As such, the above-described or illustrated ventilatory settings are not to be understood as an exclusive array, as any number of similar settings may be displayed for the clinician within the spirit of the present disclosure. Further, the described ventilatory settings are not to be understood as a necessary array, as any number of the described ventilatory settings may be appropriately replaced by other suitable ventilatory settings without departing from the spirit of the present disclosure.

Figure 3:
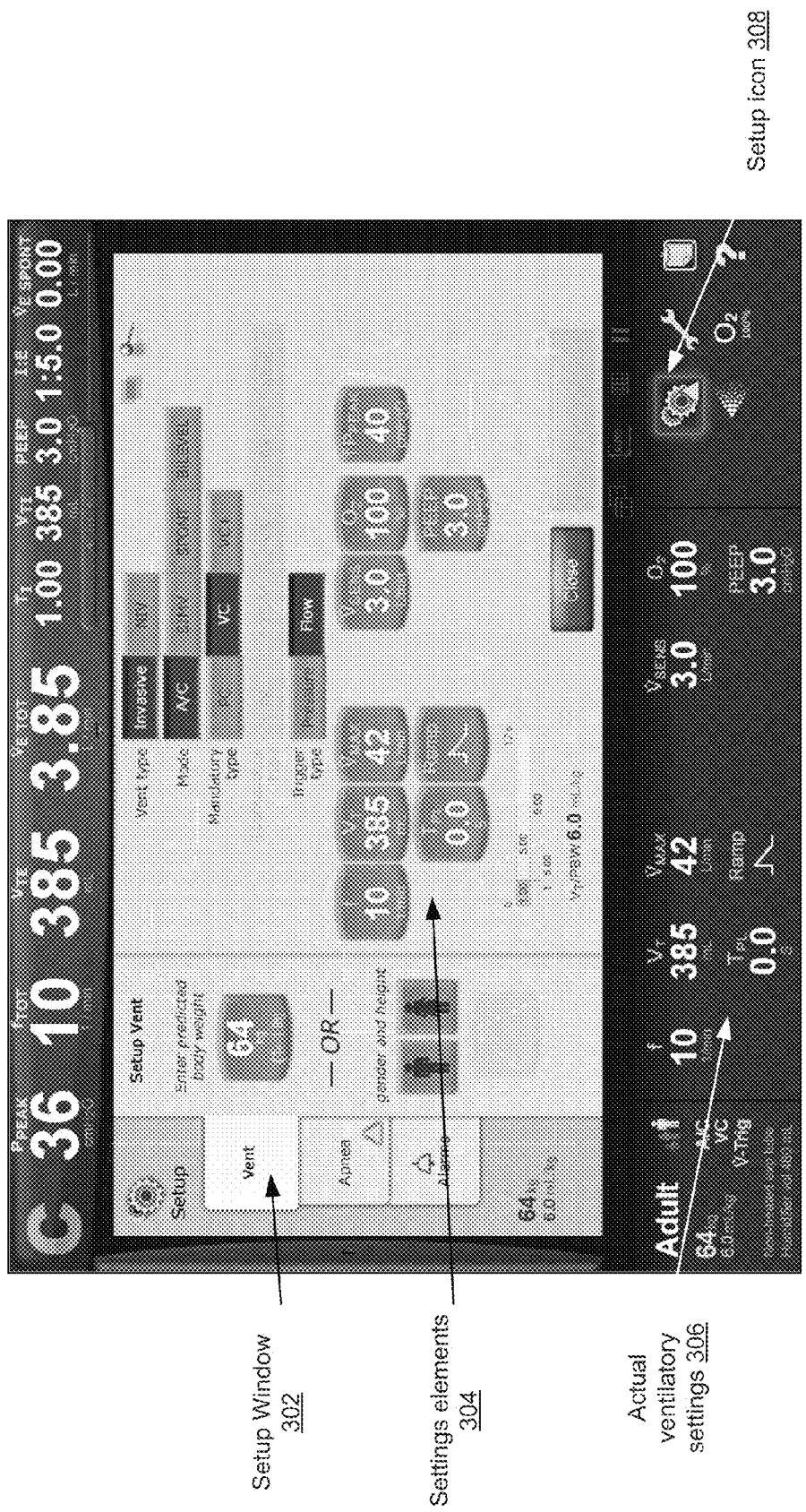
FIG. 3 is an illustration of an embodiment of a graphical user interface for displaying and accessing ventilatory settings.

FIG. 3 is an illustration of an embodiment of a graphical user interface for displaying and accessing ventilatory settings.

According to one embodiment, as illustrated in FIG. 3, a setup window 302 may be provided. Setup window 302 may be accessed by touching, clicking, or otherwise selecting an icon, such as setup icon 308, or any other setup access element. As described above, any suitable access method by which a clinician may logically and easily access setup window 302 may be provided in keeping with the present disclosure.

As illustrated, setup window 302 may include settings elements 304. A plurality of settings elements 304 may be displayed as buttons, tabs, icons, or any other suitable visual access element. The settings elements 304 may be configured in the same visual arrangement as the actual ventilatory settings 306, such that a clinician may easily correlate the actual ventilatory settings 306 with the settings elements 304 provided for adjusting them. In addition, actual settings values associated with the actual ventilatory settings 306 may be initially displayed in settings elements 304 (e.g., 10 breaths per min, 385 mL, etc.). As such, actual settings values initially displayed in settings elements 304 may be represented in a font color indicating that the values are actual settings values, for instance in a white font. Thereafter, upon display of setup window 302, a clinician may touch, click, or otherwise select one or more of the settings elements 304 in order to input or change the displayed actual settings values.

As described above, a setup icon 308 may also be provided within the GUI. As described above, the setup icon 308 may be selected for accessing setup window 302. Upon selection, setup icon 308 may further be displayed as focused. As such, setup icon 308 may offer a visual indication whenever ventilatory settings are being accessed or changed by the clinician via setup window 302.

Figure 4:
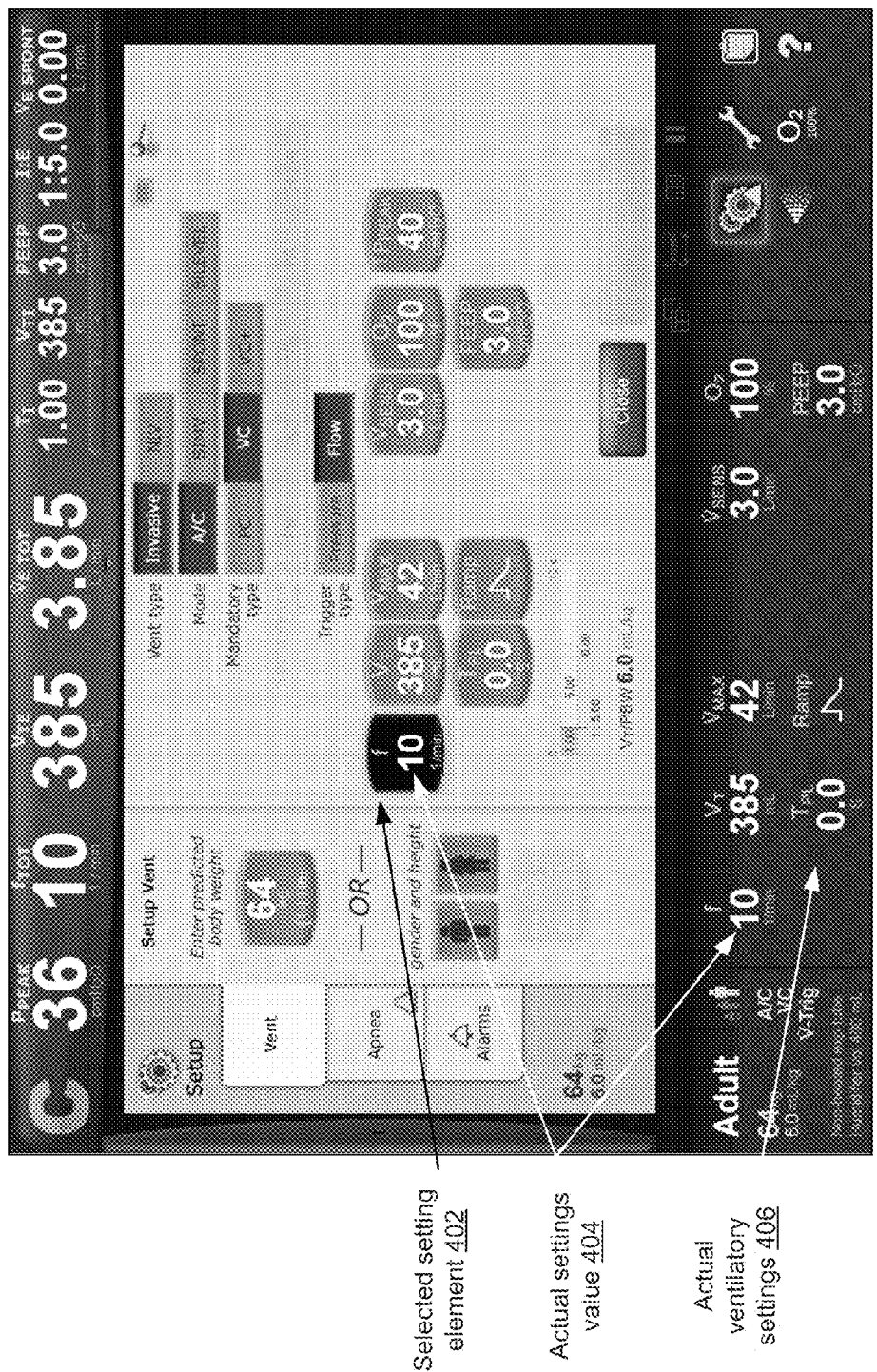
FIG. 4 is an illustration of an embodiment of a graphical user interface displaying a selected ventilatory setting element.

FIG. 4 is an illustration of an embodiment of a graphical user interface displaying a selected ventilatory setting element.

As described above, setup window 302 may provide a clinician with access to one or more settings elements. The one or more settings elements may display actual settings values corresponding to actual settings values displayed in actual ventilatory settings 406, for instance. Thereafter, a clinician may select an individual setting element, for example selected setting element 402, for adjustment. The selected setting element 402 may be identified by creation of a visual indication of selection, highlighting for example, such that it may be differentiated from unselected settings elements. As illustrated, actual setting value 404 is displayed in both the selected setting element 402 and in a corresponding frequency setting of the actual ventilatory settings 406. Indeed, selected setting element 402 may continue to display actual setting value 404 until it is changed. For example, the actual frequency setting value, i.e., 10 breaths/min, may be reproduced in selected settings element 402 unless and until the frequency setting is changed. As such, in the illustrated embodiment, the actual setting value 404 in selected setting element 402 is displayed as 10 breaths/min in a white font, indicating an actual status for the frequency setting value, unless and until it is changed.

Figure 5:
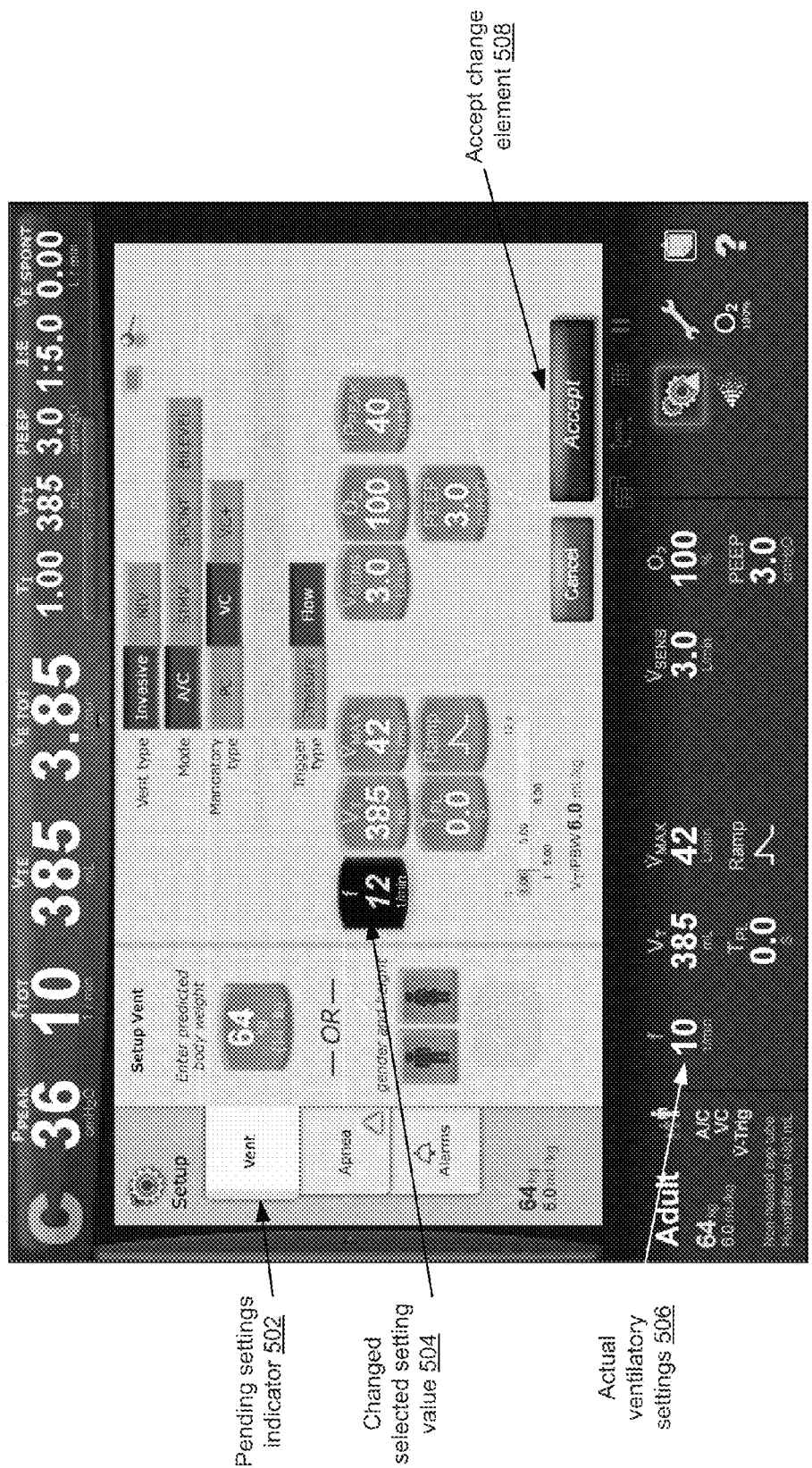
FIG. 5 is an illustration of an embodiment of a graphical user interface displaying a change to the setting value of the selected ventilatory setting element.

FIG. 5 is an illustration of an embodiment of a graphical user interface displaying a change to the setting value of the selected setting element.

In FIG. 5, the setting value of the selected setting element 402 (as described in FIG. 4) has been changed from a frequency of 10 breaths/min to a frequency of 12 breaths/min. Settings may be changed via any suitable means, for instance, via direct input into a settings input field, via use of a scroll wheel, thumbwheel, knob, mouse, or scroll bar for adjusting settings up and down, or via any other suitable device. Thus, FIG. 5 illustrates changed selected setting value 504 as 12 breaths/min. Changed selected setting value 504 may also be represented in a different font to indicate that the changed setting value has a pending status, rather than an actual status. For instance, the changed selected setting value 504 may be represented in a yellow, italicized font. In the alternative, a changed setting value may be represented in any suitable form such that the clinician may be alerted to the fact that the setting has a pending status. For instance, the changed setting value may be displayed with an asterisk, or other indication.

According to an embodiment, when one or more settings changes are pending in a setup window, screen, or page, a pending settings indicator 502 may be displayed. For example, pending settings indicator 502 is displayed as a bar along a tab associated with setup window 302. In addition, where settings changes are pending on additional screens and/or pages of the GUI, the clinician may be alerted by a similar pending settings indicator displayed along tabs associated with the additional screens and/or pages. As noted above, a clinician may be better able to identify and accept pending settings changes on multiple screens and displays of the GUI as a result innovations of the present disclosure. Note that actual ventilatory settings 506 may continue to display an actual frequency setting value, i.e., 10 breaths/min, until the pending value for changed selected setting value 504 has been accepted by the clinician.

In an embodiment, a clinician may accept a pending setting value by selecting accept change element 508. Upon accepting the pending setting value, the pending setting value may become a changed actual setting value and may automatically populate a corresponding actual ventilatory setting of the actual ventilatory settings 506.

Figure 6:
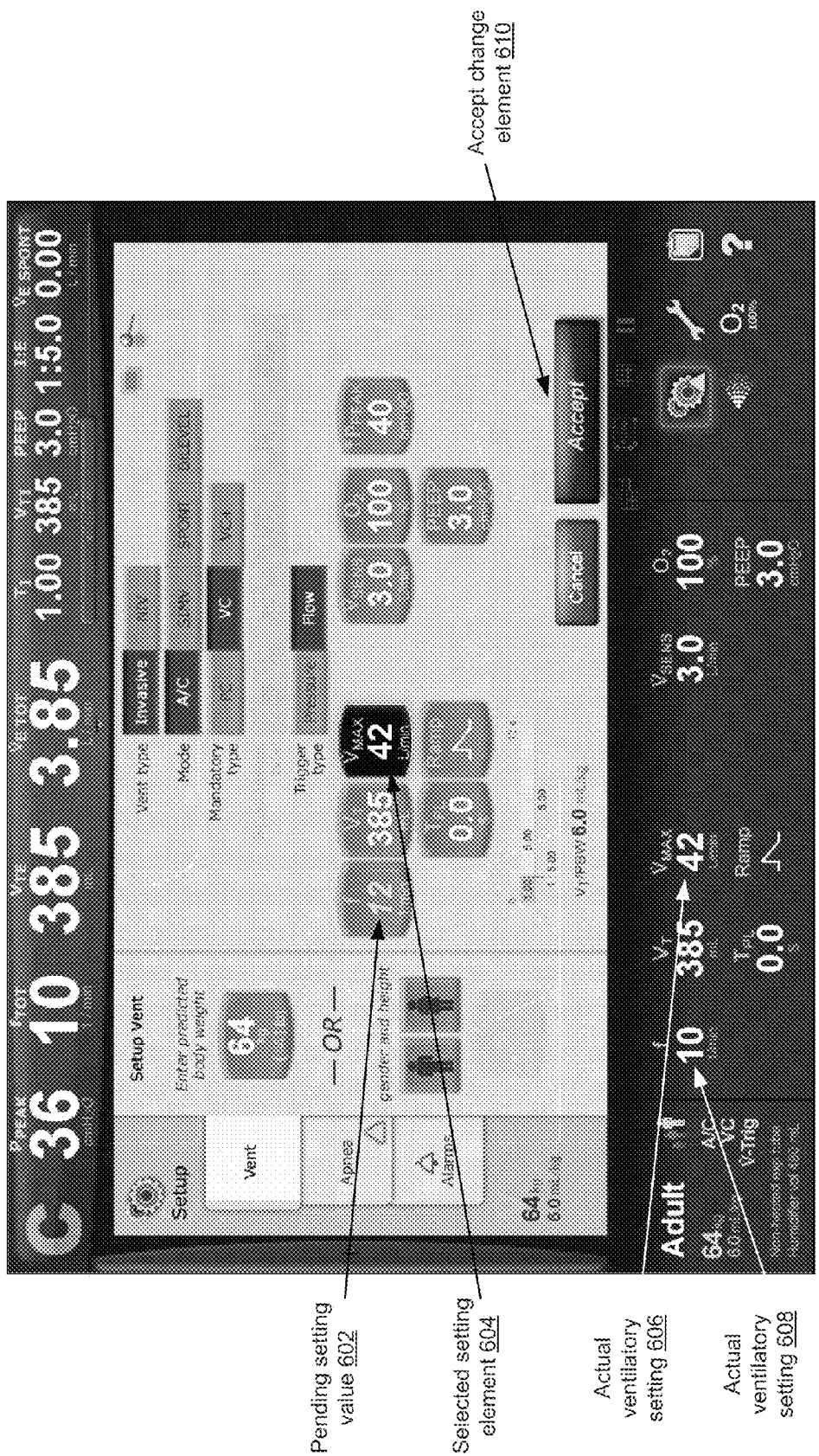
FIG. 6 is an illustration of an embodiment of a graphical user interface displaying a pending status of the change to the setting value of the selected ventilatory setting element.

FIG. 6 is an illustration of an embodiment of a graphical user interface displaying a pending status of the change to the setting value of the selected setting element.

For example, FIG. 6 illustrates a pending frequency setting change in a yellow, italicized font, i.e., pending setting value 602. In this embodiment, a setting element associated with pending setting value 602 is not shown as highlighted or selected.

According to the embodiment illustrated in FIG. 6, another setting element has been selected, i.e., selected setting element 604. As described above, selected setting element 604 continues to display an actual ventilatory setting value for maximum flow unless and until the maximum flow setting is changed. As such, the maximum flow value represented in selected setting element 604, i.e., 42 L/min, is the same as the maximum flow setting value displayed by actual ventilatory setting 606. In contrast, pending setting value 602 is 12 breaths/min, rather than the actual setting value of 10 breaths/min represented in actual ventilatory setting 608.

According to an embodiment, accept change element 610 continues to indicate that a single setting change is pending, i.e., the pending frequency value of 12 breaths/min. As such, accept change element 610 displays, for example, only "Accept."

Figure 7:
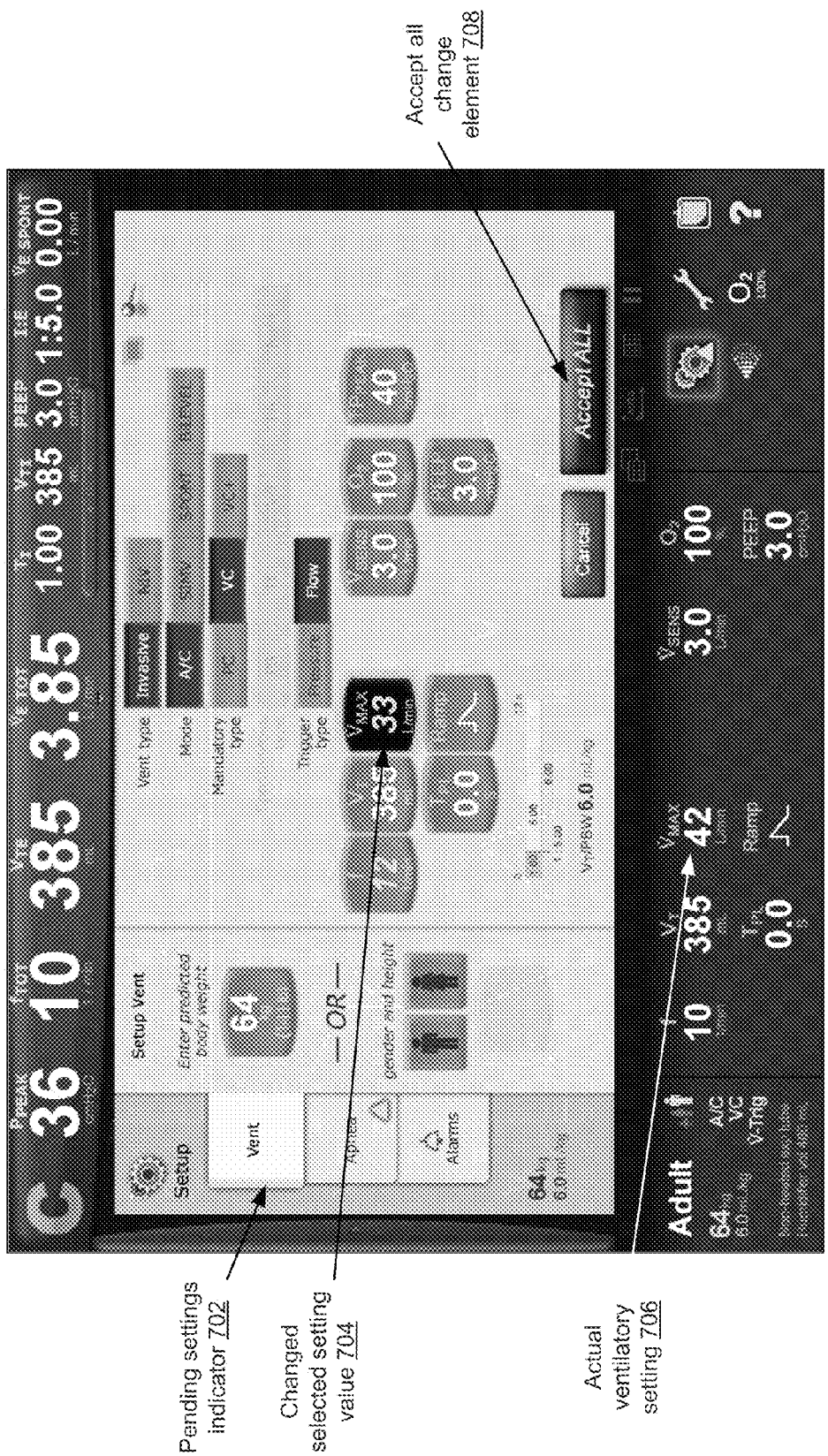
FIG. 7 is an illustration of an embodiment of a graphical user interface displaying an indicator of a plurality of pending ventilatory settings changes.

FIG. 7 is an illustration of an embodiment of a graphical user interface displaying an indicator of a plurality of pending ventilatory settings changes.

For example, FIG. 7 illustrates a setting change to an additional ventilatory setting, i.e., changed selected setting value 704. As described above, the changed setting value for maximum flow, i.e., 33 L/min, may be displayed as a pending setting value in yellow italics. Again, as described above, changed ventilatory setting value 704 is different from the actual setting value displayed in actual ventilatory setting 706 unless and until pending settings changes are accepted by the clinician.

According to an embodiment, pending settings indicator 702 may be displayed as a bar along a tab associated with setup window 302. In addition, where settings changes are pending on additional screens and/or pages of the GUI, the clinician may be alerted by a similar pending status indicator displayed along tabs associated with the additional screens and/or pages.

As illustrated in FIG. 7, when more than one setting change is pending, an accept all changes element 708 may be provided, rather than merely an accept change element (as described with reference to accept change element 610). In this case, when a clinician accepts all pending settings changes, pending changed ventilatory setting value 704 may become a changed actual value and may automatically populate actual ventilatory setting 706. Further, changed actual settings may be displayed in white font. Additionally, upon acceptance of pending settings changes, pending settings indicator 702, or other pending settings indication or icon, may be withdrawn from display.

Figure 8:
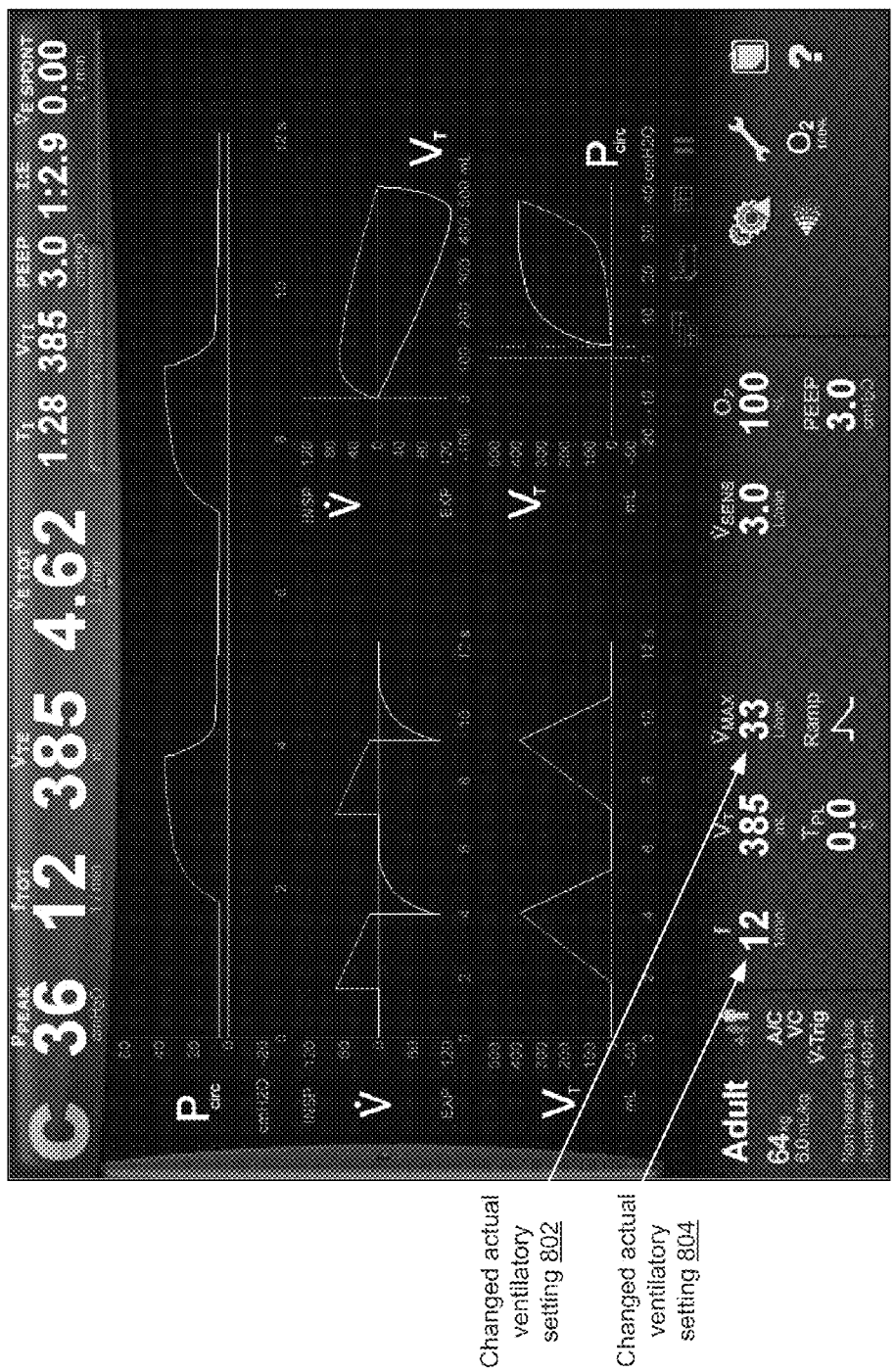
FIG. 8 is an illustration of an embodiment of a graphical user interface displaying changed actual ventilatory settings.

FIG. 8 is an illustration of an embodiment of a graphical user interface displaying changed actual ventilatory settings.

For example, FIG. 8 illustrates a GUI displaying graphical data and actual ventilatory settings, as initially described with reference to FIG. 2. However, in this case, the actual ventilatory settings have been changed vis-à-vis FIG. 2. That is, settings changes have been accepted and implemented by the ventilator, as illustrated in FIG. 8. For example, while FIG. 2 shows an actual ventilatory setting 204 with a frequency setting value of 10 breaths/min, FIG. 8 illustrates a changed actual ventilatory setting 802 with a frequency setting value of 12 breaths/min. In addition, while FIG. 2 shows an actual ventilatory setting 204 with a maximum flow value of 42 L/min, FIG. 8 illustrates a changed actual ventilatory setting 804 with a maximum flow value of 33 L/min. As described above, changed actual ventilatory settings 802 and 804 may be represented in a white font to convey to the clinician that the changed ventilatory settings have an actual status and that the changed ventilatory settings are being currently implemented by the ventilator.

The foregoing illustrated embodiments are merely examples of potential embodiments of the present disclosure. For example, rather than a setup screen, as discussed above with reference to setup window 302, a settings window or screen may be accessed. The settings window may be accessed by touching, clicking, or otherwise selecting one of a plurality of actual ventilatory settings, e.g., actual ventilatory settings 306 (as previously described with reference to FIG. 3). Actual ventilatory settings 306 may include an element for selection, for instance a button or other visual access element, or actual ventilatory settings 306 may not be associated with any visual access element, but may still be touch or selection sensitive. In this case, touching or clicking on any of the plurality of actual ventilatory settings 306 may initiate display of a settings window. These and similar methods for efficiently accessing settings elements are well within the spirit of the present disclosure.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilator comprising a display device, the ventilator configured with a computer having a processor and a memory, the memory communicatively coupled to the processor and containing instructions that, when executed by the processor, cause the ventilator to provide a graphical user interface on the display device, the graphical user interface comprising:
   a first window associated with the graphical user interface, the first window comprising:
      a plurality of actual ventilatory settings displayed according to a first visual arrangement in which each actual ventilatory setting is displayed with a size, a value and a position within the first visual arrangement; and
      a setup icon; and
   a second window concurrently displayed such that the first window is at least partially visible, wherein the second window is a setup window for adjusting the plurality of actual ventilatory settings displayed in the first window, and wherein the second window is displayed upon selection of the setup icon without displaying an intermediate setup window, the second window comprising:

a plurality of settings elements corresponding to the plurality of actual ventilatory settings, wherein each of the plurality of settings elements is selectable for adjusting a corresponding actual ventilatory setting, wherein each settings element is displayed with a size, a value and a position within the second visual arrangement that is the same as the size, the value and the position of the corresponding actual ventilatory setting within the first visual arrangement, and wherein the first visual arrangement of the first window and the second visual arrangement of the second window are concurrently visible on the graphical user interface.

2. The ventilator of claim 1, further comprising:
receiving a selection of a setting element of the plurality of settings elements; and
associating a visual indication with the selected setting element.

3. The ventilator of claim 2, wherein an actual setting value is associated with the selected setting element, and wherein the actual setting value is changed to a pending setting value that is different from the actual setting value.

4. The ventilator of claim 3, further comprising:
a visual indicator for signaling that one or more settings changes are pending.

5. The ventilator of claim 3, further comprising:
accepting the pending setting value, wherein the pending setting value becomes a changed actual setting value; and
populating a corresponding actual ventilatory setting of the plurality of actual ventilatory settings with the changed actual setting value.

6. A ventilatory system for accessing and displaying ventilatory settings, comprising:
at least one display device;
at least one processor; and
at least one memory, communicatively coupled to the at least one processor and containing instructions that, when executed by the at least one processor, provide a graphical user interface on the at least one display device, comprising:
a first window associated with the graphical user interface, the first window comprising:
a plurality of actual ventilatory settings displayed according to a first visual arrangement in which each actual ventilatory setting is displayed with a size, a value and a position within the first visual arrangement; and
a setup icon; and
a second window concurrently displayed such that the first window is at least partially visible, wherein the second window is a setup window for adjusting the plurality of actual ventilatory settings displayed in the first window, and wherein the second window is displayed upon selection of the setup icon without displaying an intermediate setup window, the second window comprising:
a plurality of settings elements corresponding to the plurality of actual ventilatory settings, wherein each of the plurality of settings elements is selectable for adjusting a corresponding actual ventilatory setting, wherein each settings element is displayed with a size, a value and a position within the second visual arrangement that is the same as the size, the value and the position of the corresponding actual ventilatory setting within the first visual arrangement, and wherein the first visual arrangement of the first window and the second visual arrangement of the second window are concurrently visible on the graphical user interface.

7. The ventilatory system of claim 6, wherein the plurality of actual ventilatory settings are selectable.

8. The ventilatory system of claim 7, wherein selection of at least one of the plurality of actual ventilatory settings accesses at least one of the plurality of settings elements.

9. The ventilatory system of claim 8, further comprising:
receiving a selection of a setting element of the plurality of settings elements; and
associating a visual indication with the selected setting element.

10. The ventilatory system of claim 9, wherein an actual setting value is associated with the selected setting element, and wherein the actual setting value is changed to a pending setting value that is different from the actual setting value.

11. The ventilatory system of claim 10, further comprising:
accepting the pending setting value, wherein the pending setting value becomes a changed actual setting value; and
populating a corresponding actual ventilatory setting of the plurality of actual ventilatory settings with the changed actual setting value.

12. A non-transitory computer-readable storage medium having instructions that when executed provide a graphical user interface for accessing and displaying ventilatory settings, the graphical user interface comprising:
a first window associated with the graphical user interface, the first window comprising:
a plurality of actual ventilatory settings displayed according to a first visual arrangement in which each actual ventilatory setting is displayed with a size, a value and a position within the first visual arrangement; and
a setup icon; and
a second window concurrently displayed such that the first window is at least partially visible, wherein the second window is a setup window for adjusting the plurality of actual ventilatory settings displayed in the first window, and wherein the second window is displayed upon selection of the setup icon without displaying an intermediate setup window, the second window comprising:
a plurality of settings elements corresponding to the plurality of actual ventilatory settings, wherein each of the plurality of settings elements is selectable for adjusting a corresponding actual ventilatory setting, wherein each settings element is displayed with a size, a value and a position within the second visual arrangement that is the same as the size, the value and the position of the corresponding actual ventilatory setting within the first visual arrangement, and wherein the first visual arrangement of the first window and the second visual arrangement of the second window are concurrently visible in the graphical user interface.

13. The non-transitory computer-readable storage medium of claim 12, wherein selection of at least one of the plurality of actual ventilatory settings accesses at least one of the plurality of settings elements.

14. The non-transitory computer-readable storage medium of claim 12, further comprising:
receiving a selection of a setting element of the plurality of settings elements; and
associating a visual indication with the selected setting element.

15. The non-transitory computer-readable storage medium of claim 14, wherein an actual setting value is associated with the selected setting element, and wherein the actual setting value is changed to a pending setting value that is different from the actual setting value.

16. The non-transitory computer-readable storage medium of claim 15, further comprising:
   accepting the pending setting value, wherein the pending setting value becomes a changed actual setting value; and
   populating a corresponding actual ventilatory setting of the plurality of actual ventilatory settings with the changed actual setting value.

17. The non-transitory computer-readable storage medium of claim 12, wherein the non-transitory computer-readable storage medium is selected from a group consisting of: RAM, ROM, EPROM, EEPROM, flash memory, CD-ROM, DVD, magnetic cassettes, magnetic tape, and magnetic disk storage.

18. The ventilator of claim 3, wherein the selected setting element displays the actual setting value in one font color, and wherein the selected setting element displays the pending setting value in another font color.

19. The ventilatory system of claim 10, wherein the selected setting element displays the actual setting value in one font color, and wherein the selected setting element displays the pending setting value in another font color.

20. The non-transitory computer-readable storage medium of claim 15, wherein the selected setting element displays the actual setting value in one font color, and wherein the selected setting element displays the pending setting value in another font color.

* * * * *